(12) United States Patent
Alper

(10) Patent No.: US 8,519,104 B2
(45) Date of Patent: Aug. 27, 2013

(54) MONOCLONAL ANTIBODIES AGAINST GMF-B ANTIGENS, AND USES THEREFOR

(75) Inventor: Ozge Alper, Bethesda, MD (US)

(73) Assignee: Alper Biotech, LLC, Rockville, MD (US)

( * ) Notice: Subject to any disclaimer, the term of this patent is extended or adjusted under 35 U.S.C. 154(b) by 391 days.

(21) Appl. No.: 12/944,510

(22) Filed: Nov. 11, 2010

(65) Prior Publication Data
US 2011/0136148 A1 Jun. 9, 2011

Related U.S. Application Data

(60) Provisional application No. 61/260,716, filed on Nov. 12, 2009.

(51) Int. Cl.
*C07K 16/00* (2006.01)
*G01N 33/53* (2006.01)

(52) U.S. Cl.
USPC ................. 530/387.1; 424/178.1; 435/7.1

(58) Field of Classification Search
None
See application file for complete search history.

(56) References Cited

U.S. PATENT DOCUMENTS

| | | |
|---|---|---|
| 5,270,452 A | 12/1993 | Lim et al. |
| 7,705,120 B2 | 4/2010 | Lillie et al. |
| 2008/0182246 A1 | 7/2008 | Wang et al. |
| 2008/0293162 A1 | 11/2008 | Alper |
| 2010/0210738 A1 | 8/2010 | Leyland-Jones et al. |

FOREIGN PATENT DOCUMENTS

WO 2008/030845 A2 3/2008

OTHER PUBLICATIONS

Yamazaki et al. (Histopathology, vol. 47, No. 3, pp. 292-302, Sep. 2005).*
Kaplan et al., "Molecular Cloning and Expression of Biologically Active Human Glia Maturation Factor-β," *Journal of Neurochemistry*, 57(2):483-490 (1991).
Li et al., "Identification of glia maturation factor beta as an independent prognostic predictor for serous ovarian cancer," *European J Cancer* 46:2104-2118 (2010).
Lim et al., "Glia maturation factor-beta promotes the appearance of large neurofilament-rich neurons in injured rat brains," *Brain Research* 504:154-158 (1989).
Lim et al., "Endogenous immunoreactive glia maturation factor-like molecule in astrocytes and glioma cells," *Developmental Brain Research* 33:49-57 (1987).
Lim et al., "Distribution of immunoreactive glia maturation factor-like molecule in organs and tissues," *Developmental Brain Research* 33:93-100 (1987).
Lim et al., "Endogenous immunoreactive glia maturation factor-like molecule in cultured rat Schwann cells," *Developmental Brain Research* 40:277-284 (1988).
Lim et al., "Purification of Glia Maturation Factor," *Methods in Enzymology* 147:225-235 (1987).
Lim et al., "Activation of Nuclear Factor-κB in C6 Rat Glioma Cells After Transfection with Glia Maturation Factor," *Journal of Neurochemistry* 74(2):596-602 (2000).
Menon et al., "Diminished degradation of myelin basic protein by anti-sulfatide antibody and interferon-γ in myelin from glia maturation factor-deficient mice," *Neuroscience Research* 58:156-163 (2007).
Nieto-Sampedro et al., "Early release of glia maturation factor and acidic fibroblast growth factor after rat brain injury," *Neuroscience Letters* 86:361-365 (1988).
Pantazis et al., "Transfection of C6 glioma cells with glia maturation factor upregulates brain-derived neurotrophic factor and nerve growth factor: trophic effects and protection against ethanol toxicity in cerebellar granule cells," *Brain Research* 865:59-76 (2000).
Ryken et al., "Induction of Cytoskeletal Alterations in C6 Glioma by Glia Maturation Factor," *Int. J. Devl. Neuroscience* 5(3):215-225 (1987).
Yamazaki et al., "Glia maturation factor-β is produced by thymoma and may promote intratumoral T-cell differentation," *Histopathology* 47:292-302 (2005).
Zaheer et al., "Diminished cytokine and chemokine expression in the central nervous system of GMF-deficient mice with experimental autoimmune encephalomyelitis," *Brain Research* 1144:239-247 (2007).
Zaheer et al., "Enhanced expression of neurotrophic factors by C6 rat glioma cells after transfection with glia maturation factor," *Nueroscience Letters* 265:203-206 (1999).
Zaheer et al., "A novel role of glia maturation factor: induction of granulocyte-macrophage colony-stimulating factor and pro-inflammatory cytokines," *Journal of Neurochemistry* 101:364-376 (2007).
Choi et al., "Triple-Negative, Basal-Like, and Quintuple-Negative Breast Cancers; Better Prediction Model for Survival," *BMC Cancer* 10:507-522 (2010).
Inagaki et al., "Sensitive immunoassays for human and rat GMFB and GMFG, tissue distribution and age-related changes," *Biochimica Et Biophysica Acta*, 3:208-216 2004).

(Continued)

*Primary Examiner* — Laura B Goddard
*Assistant Examiner* — Meera Natarajan
(74) *Attorney, Agent, or Firm* — Finnegan, Henderson, Farabow, Garrett & Dunner, LLP

(57) ABSTRACT

The disclosure relates to monoclonal antibodies (mAbs) preferentially selective for soluble GMF-B (sGMF-B) antigens or for sGMF-B as well as other forms of GMF-B, hybridoma lines that secrete these antibodies or fragments thereof, and the use of such antibodies and antibody fragments to preferentially detect sGMF-B antigens, including for example those expressed by cancer cells or in patients with cancer or dementia. Other aspects of the present disclosure relate to antibodies that are specific to or demonstrate preferential binding to a soluble or secreted form of GMF-B. Yet other aspects relate to antibodies or antibody fragments that are capable of reducing the activity of GMF-B in at least one form, including a soluble form or a secreted form. The present disclosure further relates to monoclonal, chimeric antibodies and fragments thereof, processes for producing such antibodies and their fragments, and their therapeutic and diagnostic uses, including in the treatment and detection of cancer, e.g., human breast, ovary, head, neck, and brain, and dementia. Methods and kits for the immunodetection and immunotherapy of cells or samples which express sGMF-B antigens, e.g., from patient and non-patient samples, are also disclosed.

18 Claims, 26 Drawing Sheets

(56) References Cited

OTHER PUBLICATIONS

Speers, C., "Novel Strategies for the Treatment of Estrogen Receptor-Negative Breast Cancer," Government Grant, Award No. W81XWH-06-1-0715, Apr. 2009.

Wang et al., "Gene-Expression Profiles to Predict Distant Metastasis of Lymph-Node Negative Primary Breast Cancer," *The Lancet* 365:671-679 (2005).

International Search Report mailed Dec. 1, 2011, in PCT/US2010/056399.

International Search Report mailed Dec. 12, 2012, in PCT/US2012/037327.

Wang, et al., "Polyclonal antibody localizes glia maturation factor beta-like immunoreactivity in neurons and glia," *Brain Research*, 1:1-7 (1992).

Walker, et al., "Immunohistochemical markers as predictive tools for breast cancer," *Journal of Clinical Pathology*, 6:689-696 (2008).

Tapiola Tero, et al., Cerebrospinal fluid {beta}-amyloid 42 and tau proteins as biomarkers of Alzheimer-type pathologic changes in the brain, *Archives of Neurology*, 3:382-389 (2009).

Written Opinion of the International Searching Authority mailed May 15, 2012, in PCT/US2010/056399.

Written Opinion of the International Searching Authority mailed Dec. 12, 2012, in PCT/US2012/037327.

Zaheer et al. "Glia maturation factor modulates beta-amyloid-induced glial activation, inflammatory cytokine/chemokine production and neuronal damage" Brain Research (2008) 1208:192-203.

Alper BioTech, "AB-Glia Maturation Factor-beta (GMF) IHC Kit for immunohistochemical staining of GMFbeta in FFPE Tissue," released Apr. 2011 in Alper BioTech Kit, Catalog No. AB01, 4 pages.

* cited by examiner

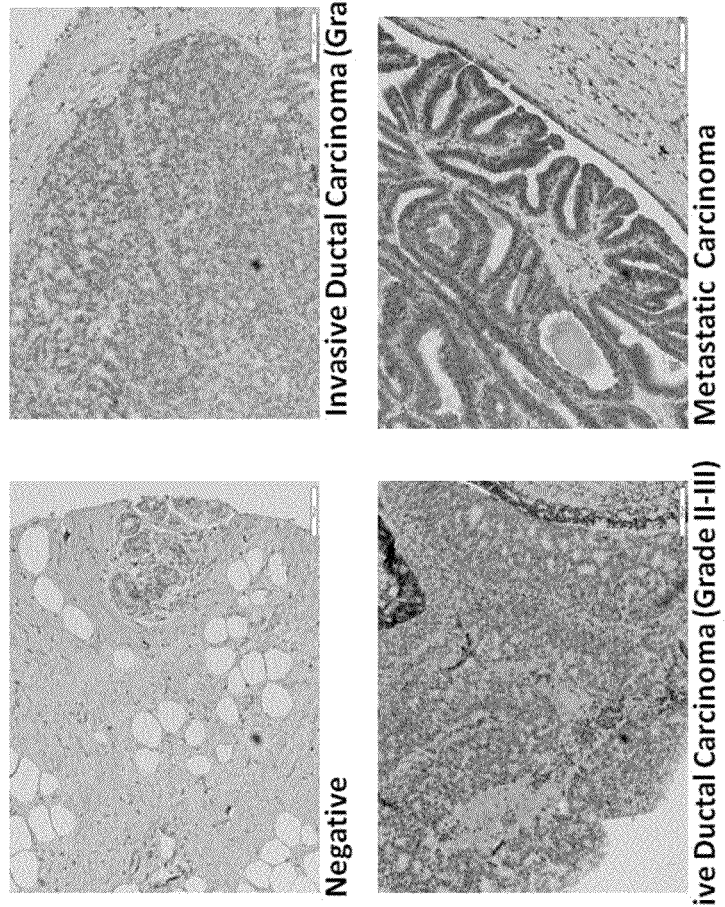
FIGURE-3(A). Immunostaining of GMFB in Breast Cancer Tissues (10x)

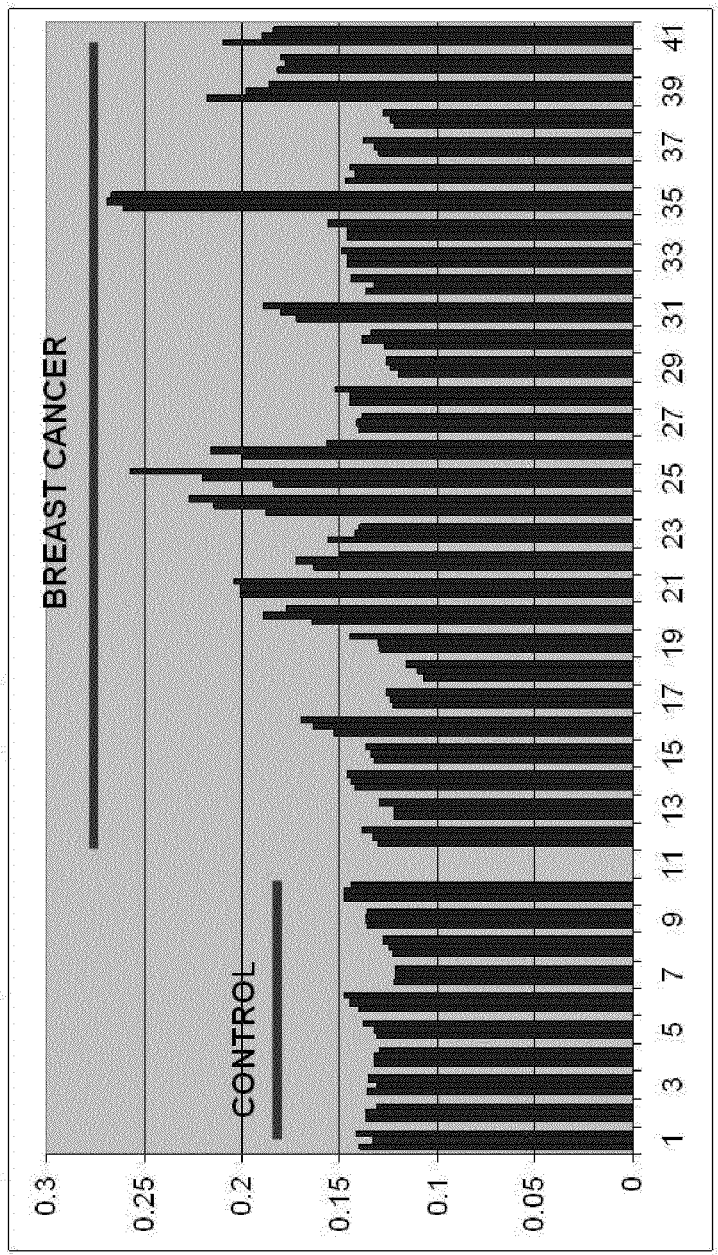

FIGURE 6(A).

| ID | Diagnosis | category | Seen longitudinally by ADRC | ApoE Status | gender | race | Age at onset | Age at blood draw | Year of Diagnosis | ALPER/AD data ORDER |
|---|---|---|---|---|---|---|---|---|---|---|
| 888350 | Prob AD | early | yes | 3/3 | female | Caucasian | 67 | 68 | 2008 | 9 |
| 887854 | Prob AD | early | yes | 4/4 | male | African-American | 72 | 73 | 2008 | 1 |
| 887502 | Prob AD | early | | 4/4 | female | Caucasian | 72 | 73 | 2009 | 16 |
| 883254 | Prob AD | late | | 3/3 | male | Caucasian | 66 | 78 | 2005 | 2 |
| 883262 | Prob AD | late | | 3/4 | female | African-American | 65 | 78 | 2007 | 12 |
| 884382 | Prob AD | late | | 3/3 | male | Caucasian | 68 | 85 | 2005 | 7 |
| 888680 | Prob AD | mid | | 3/3 | female | Caucasian | 63 | 69 | 2009 | 13 |
| 886677 | Prob AD | mid | | 3/4 | female | African-American | 70 | 76 | 2009 | 14 |
| 886732 | Prob AD | mid | | 3/4 | female | African-American | 68 | 75 | 2006 | 6 |
| 887651 | Prob AD | mid | | 3/4 | female | Caucasian | 71 | 78 | 2009 | 5 |
| 887271 | Control | control | yes | 3/3 | male | Caucasian | | 68 | 2006 | 11 |
| 884184 | Control | control | | 2/3 | female | African-American | | 73 | 2009 | 15 |
| 885596 | Control | control | | 2/4 | male | African-American | | 78 | 2006 | 17 |
| 884345 | Control | control | yes | 3/3 | female | Caucasian | | 69 | 2008 | 4 |
| 888365 | Control | control | yes | 3/4 | male | African-American | | 75 | 2007 | 8 |
| 887761 | Control | control | yes | 3/3 | male | Caucasian | | 76 | 2007 | 3 |
| 885539 | Control | control | | 3/3 | female | Caucasian | | 78 | 2009 | 10 |

Figure 7(A).

```
GMF-B H-Chain
BLASTN 2.2.20 [Feb-08-2009]
Database: igallncseq 530 sequences; 154,952 total letters
Query= tmpseq_0  (1274 letters)

Score      E
Sequences producing significant alignments:                         (bits)   Value
IGHV1-2*02                                                            240    8e-65
IGHV1-2*03                                                            238    2e-64
IGHV1-2*04                                                            237    7e-64
IGHV1-18*01                                                           237    7e-64
IGHV1-3*01                                                            237    7e-64
IGHV1-3*02                                                            230    5e-62
IGHV1-f*01                                                            229    2e-61
IGHV1-69*10                                                           227    5e-61
IGHV1-46*03                                                           227    5e-61
IGHV1-46*01                                                           227    5e-61
Domain classification requested: Kabat system
```

```
                                              |-----------------------------FWR1-----------------------------
                                              V  Q  L  Q  Q  S  G  P  E  L  V  K  K  P  G  A  S  V  K  M  S  C  K
ID%                                           GAGGTCCAGCTGCAGCAGTCTGGACCTGAGCTGGTAAAGCCTGGGGCTTCAGTGAAGATGTCCTGCAAGG  117
                tmpseq_0   48                 V  Q  L  V  Q  S  G  A  E  V  K  K  P  G  A  S  V  K  V  S  C  K
76.1(223/293)   IGHV1-2*02   2                -.....G.............GT....GG.....G..AAG..................G.C........   70
75.8(222/293)   IGHV1-2*03   2                -.....G.............GT....GG.....G..AAG..................G.C........   70
75.8(222/293)   IGHV1-2*04   2                -.....G.............GT....GG.....G..AAG.T................G.C........   70
100(10/10)      IGHD3-16*02
100(10/10)      IGHD3-16*01
90.0(9/10)      IGHD7-27*01
100(24/24)      IGHJ6*02
87.5(28/32)     IGHJ4*03
75.8(222/293)   IGHV1-18*01  2                -.....T.............GT....G......G..AAG..................G.C........   70
75.8(222/293)   IGHV1-3*01   2                -...................TGT...GG.....G..AAG..................G.T........   70
75.1(220/293)   IGHV1-3*02   2                -.....T.............GT....GG.....G..AAG..................G.T........   70
75.0(219/292)   IGHV1-f*01   1                -.................GTA.....GG.....G..AAG.............A....A.C........   70
74.7(219/293)   IGHV1-69*10  2                -.....G.............GT....GG.....G..AAG............T.C...G.C........   70
74.7(219/293)   IGHV1-46*03  2                -.....G.............GT....GG.....G..AAG..................G.T........   70
74.7(219/293)   IGHV1-46*01  2                -.....G.............GT....GG.....G..AAG..................G.T........   70
```

Figure 7(B).

```
                           <--------->  <-----CDR1----->                    <------FWR2-----
                           A S G Y T F T  S Y V M H                    W V K Q K P G Q G L E W
                           CTTCTGGATACACATTCACT AGCTATGTTATGCAC  TGGGTGAAGCAGAGCAGGCCTGGGCAGGGCCTTGAGTG  187
                           A S G Y T F T  G Y Y M H             W V R Q A P G Q G L E W

ID%      tmpseq_0    118
76.1 (223/293) IGHV1-2*02   71  ........C..........  G......CTA........  ...........CGA.....GCC.......A..A..G......  140
75.8 (222/293) IGHV1-2*03   71  ........C..........  G......CTA........  ...........CNA.....GCC.......A..A..G......  140
75.8 (222/293) IGHV1-2*04   71  ........C..........  G......CTA........  ...........CGA.....GCC.......A..A..G......  140
100 (10/10)    IGHD3-16*02      -------------------  ------------------  ------------------------------------------
100 (10/10)    IGHD3-16*01      -------------------  ------------------  ------------------------------------------
90.0 (9/10)    IGHD7-27*01      -------------------  ------------------  ------------------------------------------
100 (24/24)    IGHJ6*02         -------------------  ------------------  ------------------------------------------
87.5 (28/32)   IGHJ4*03         -------------------  ------------------  ------------------------------------------
75.8 (222/293) IGHV1-18*01  71  .......T..C..T..C..  .......G...CAG....  ...........CGA.....GCC.......A..A..G......  140
75.8 (222/293) IGHV1-3*01   71  ..........C........  ..........T.......  ...........CGC.....GCC...C...A..AA.G......  140
75.1 (220/293) IGHV1-3*02   71  ..........C........  ..........T.......  ...........CGC.....GCC...C...A..AA.G......  140
75.0 (219/292) IGHV1-f*01   71  T.........C........  GA....CTAC........  ...........C.A.....GCC.......AA.A..G......  140
74.7 (219/293) IGHV1-69*10  71  .....GG...C......GC  .......C...CAG....  ...........CGA.....GCC.......A..A..G......  140
74.7 (219/293) IGHV1-46*03  71  .A........C........  G......CTA........  ...........CGA.....GCC.......A..A..G......  140
74.7 (219/293) IGHV1-46*01  71  .A........C........  G......CTA........  ...........CGA.....GCC.......A..A..G......  140
```

Figure 7(C).

| ID% | | | | | | |
|---|---|---|---|---|---|---|
| | tmpseq_0 | 188 | `GATTGGA`<br>`  I  G`<br>`  M  G` | `TATATTAATCCTTACAATGAAGGAACTAAGTACAATGAGAAGTTCAAAGGC`<br>`<------------CDR2-----------`<br>`  Y  I  N  P  Y  N  E  G  T  K  Y  N  E  K  F  K  G`<br>`  W  I  N  P  N  S  G  G  T  N  Y  A  Q  K  F  Q  G` | `AAGGCCACACTG` 257<br>`<----------`<br>`  K  A  T  L`<br>`  R  V  T  M` |
| 76.1 (223/293) | IGHV1-2*02 | 141 | ....G... | .GG..C..C...A...G..GT..C..A..C.TGCAC.......TC.G... | .G..T...CA... 210 |
| 75.8 (222/293) | IGHV1-2*03 | 141 | ....G... | .GG..C..C...A...G..GT..C..A..C.TGCAC.......TC.G... | .G..T...CA... 210 |
| 75.8 (222/293) | IGHV1-2*04 | 141 | ....G... | .GG..C..C...A...G..GT..C..A..C.TGCAC.......TC.G... | TG..T...CA... 210 |
| 100 (10/10) | IGHD3-16*02 | | | | |
| 100 (10/10) | IGHD3-16*01 | | | | |
| 90.0 (9/10) | IGHD7-27*01 | | | | |
| 100 (24/24) | IGHJ6*02 | | | | |
| 87.5 (28/32) | IGHJ4*03 | | | | |
| 75.8 (222/293) | IGHV1-18*01 | 141 | ....G... | .GG..C.GCG.........GTAAC..A..C.TGCAC........C..C.G... | .GA.T...CA... 210 |
| 75.8 (222/293) | IGHV1-3*01 | 141 | ....G... | .GG..C..CG..GG.....GTAAC..A..A.TTCAC........C..C.G... | .GA.T...CA.T. 210 |
| 75.1 (220/293) | IGHV1-3*02 | 141 | ....G... | .GG.GC..CG..GG.....GTAAC..A..A.TTCAC.G......C..C.G... | .GA.T...CA.T. 210 |
| 75.0 (219/292) | IGHV1-f*01 | 141 | ....G... | CT.G.G..G...G.AG...GT.A...A..TA...GCA........C..C.G... | .GA.T...CA.A. 210 |
| 74.7 (219/293) | IGHV1-69*10 | 141 | ....G... | .GG..C.TC...AT.CT..GTAT.G.A..C...GCAC........C..C.G... | .GA.T...GA.T. 210 |
| 74.7 (219/293) | IGHV1-46*03 | 141 | ....G... | ATA..C..C...AGTGG..GTA.C..A.GC...GCAC........C..C.G... | .GA.T...CA... 210 |
| 74.7 (219/293) | IGHV1-46*01 | 141 | ....G... | ATA..C..C...AGTGG..GTA.C..A.GC...GCAC........C..C.G... | .GA.T...CA... 210 |

| ID% | Name | Start | Y Y C A R<br>ATTATTGTGCAAGA | CDR3 →<br>S T M I T T G F A Y W G Q G T T V T<br>TCGACTATGATTACGACGGGGTTTGCTTACTGGGGCCAAGGGACCACGGTCAC | End | SID |
|---|---|---|---|---|---|---|
|  | tmpseq_0 | 328 | ATTATTGTGCAAGA | TCGACTATGATTACGACGGGGTTTGCTTACTGGGGCCAAGGGACCACGGTCAC | 394 | (SID 21) |
| 76.1 (223/293) | IGHV1-2*02 | 281 | .....C.....G... | ---------------------------------------------------- | 294 | (SID 20) |
| 75.8 (222/293) | IGHV1-2*03 | 281 | .....C.....G... | ---------------------------------------------------- | 294 | (SID 23) |
| 75.8 (222/293) | IGHV1-2*04 | 281 | .....C.....G... | ---------------------------------------------------- | 294 | (SID 22) |
| 100 (10/10) | IGHD3-16*02 | 5 | -------------- | ..............--------------------------------------- | 14 | (SID 24) |
| 100 (10/10) | IGHD3-16*01 | 5 | -------------- | ..............--------------------------------------- | 14 | (SID 25) |
| 90.0 (9/10) | IGHD7-27*01 | 1 | -------------- | .A............--------------------------------------- | 10 | (SID 26) |
| 100 (24/24) | IGHJ6*02 | 29 | -------------- | -----------------------....AC........................ | 52 | (SID 27) |
| 87.5 (28/32) | IGHJ4*03 | 6 | -------------- | -------------------------........CT.................. | 37 | (SID 28) |
| 75.8 (222/293) | IGHV1-18*01 | 281 | .....C.....G... | ---------------------------------------------------- | 294 | (SID 29) |
| 75.8 (222/293) | IGHV1-3*01 | 281 | .....C.....G... | ---------------------------------------------------- | 294 | (SID 30) |
| 75.1 (220/293) | IGHV1-3*02 | 281 | .....C.....G... | ---------------------------------------------------- | 294 | (SID 31) |
| 75.0 (219/292) | IGHV1-f*01 | 281 | .....C.....:... | ---------------------------------------------------- | 292 | (SID 32) |
| 74.7 (219/293) | IGHV1-69*10 | 281 | .....C.....T... | ---------------------------------------------------- | 294 | (SID 33) |
| 74.7 (219/293) | IGHV1-46*03 | 281 | .....C.....G... | ---------------------------------------------------- | 294 | (SID 34) |
| 74.7 (219/293) | IGHV1-46*01 | 281 | .....C.....G... | ---------------------------------------------------- | 294 | (SID 35) |

Figure 8(A)

GMF-B Kappa-Chain

```
BLASTN 2.2.20 [Feb-08-2009]
Database: igallncseq 530 sequences; 154,952 total letters
Query= tmpseq_0  (1313 letters)

Sequences producing significant alignments:
                                                    Score    E
                                                   (bits) Value
IGKV1D-33*01                                         265   3e-72
IGKV1-33*01                                          265   3e-72
IGKV1-27*01                                          240   9e-65
IGKV1D-43*01                                         233   6e-63
IGKV1-NL1*01                                         230   6e-62
A4a                                                  229   2e-61
IGKV1-6*01                                           224   4e-60
IGKV1-17*02                                          224   4e-60
IGKV1-16*01                                          224   4e-60
IGKV1D-13*01                                         224   4e-60

Domain classification requested: Kabat system
```

```
ID%                                  <----------------------------------FWR1------------------------------->
                                     D  I  L  M  T  Q  S  P  S  S  L  S  A  S  L  G  G  K  V  T  I  T  C
                                     GACATTCTGATGACCCAGTCTCCATCCTCACTGTCTGCATCTCTGGGAGGCAAAGTCACCATCACTTGC
              tmpseq_0           28  D  I  Q  M  T  Q  S  P  S  S  L  S  A  S  V  G  D  R  V  T  I  T  C
80.1(225/281) IGKV1D-33*01        1  .....C.A...........................................GA....A.G.......A  C
80.1(225/281) IGKV1-33*01         1  .....C.A...........................................GA....A.G.......A  C
78.0(213/273) IGKV1-27*01         1  .....C.A.........................C.................GA....A.G.......A  C
86.8(33/38)   IGKJ1*01                                                                                    -
88.2(30/34)   IGKJ4*02                                                                                    -
77.1(212/275) IGKV1D-43*01        3  .....C.G.........................T.C................GA....A.G.......T  C
76.5(212/277) IGKV1-NL1*01        1  .....C.A.........................C..................GA....A.G.......C  C
77.4(212/274) A4a                 1  .....C.A.........................C..................GA....A.G.......C  C
75.8(210/277) IGKV1-6*01          3  .....C.A.........................C..................GA....A.G.......C  C
75.8(210/277) IGKV1-17*02         1  .....C.A.T...............................................GA....A.G.......C  C
75.8(210/277) IGKV1-16*01         1  .....C.A.........................C..................GA....A.G....T..C  C
75.8(210/277) IGKV1D-13*01        3  .....C.A.T...............................................GA....A.G.......C  C
```

Figure 8(B)

| ID% | | | <----------CDR1----------> | <-----------------------------------FWR2-----------------------------------> | |
|---|---|---|---|---|---|
| | | | K A S Q D I N K Y I A | W Y Q H K P G E G P R L L | |
| | tmpseq_0 | 98 | AGGCAAGCCAAGACATTAACAAGTATATAGCT | TGGTACCAACACAAGCCTGGAGAAGGTCCTAGGCTGCT | 167 |
| | | | Q A S Q D I S N Y L N | W Y Q Q K P G K A P K L L | |
| 80.1 (225/281) | IGKV1D-33*01 | 71 | ...G..T..G......G...C....T..AA. | ...T..G..G..A..A..GA....CC....A...C.. | 140 |
| 80.1 (225/281) | IGKV1-33*01 | 71 | ...G..T..G......G...C....T..AA. | ...T..G..G..A..A..GA....CC....A...C.. | 140 |
| 78.0 (213/273) | IGKV1-27*01 | 71 | ...G..T..G.G....G...T....T....C | ...T..G..G..A..A..GA....T.....A...C.. | 140 |
| 86.8 (33/38) | IGKJ1*01 | | | | |
| 88.2 (30/34) | IGKJ4*02 | | | | |
| 77.1 (212/275) | IGKV1D-43*01 | 71 | G....C..T..G.G......G..GT..T....C | ...T..G..A..A.A.C.A....CC....A....CT.. | 140 |
| 76.5 (212/277) | IGKV1-NL1*01 | 71 | G....G..T..G.G......G...T.C.T....C | ...T..G..G..A..A..GA....CC....A...C.. | 140 |
| 77.4 (212/274) | A4a | 71 | G....G..T..G.G......G...T....T....C | ...T..G..G..A..A..GA....T.....A...C.. | 140 |
| 75.8 (210/277) | IGKV1-6*01 | 71 | G....G..T..G.G......GA..TG..T....GC | ...T..G..G..A..A..GA....CC....A...C.. | 140 |
| 75.8 (210/277) | IGKV1-17*02 | 71 | G....G..T..G.G......GA..TG..T....GC | ...T..G..G..A..A..GA....CC....A..GC.. | 140 |
| 75.8 (210/277) | IGKV1-16*01 | 71 | G....G..T..G.G......G...T....T....C | ...TT.G..G..A..A..GA....CC....A.TCC.. | 140 |
| 75.8 (210/277) | IGKV1D-13*01 | 71 | G....G..T..G.G......G..GTGC.T....C | ...T..G..G..A..A..GA.....C....A...C.. | 140 |

| ID% | | FWR3 | CDR3 |
|---|---|---|---|
| | | Y S F S I T N L E P E D I A T Y Y C | L Q Y D N |
| | tmpseq_0 | TTATTCCTTCAGCATCACCAACCTGGAACCTGAAGATATTGCAACTTATTATTGT 237 | CTACAGTATGATAAT 306 |
| | | F T F T I S S L Q P E D I A T Y Y C | Q Q Y D N |
| 80.1 (225/281) | IGKV1D-33*01 | ...T.A.T...C.........G..G....C.G..............A... 210 | .A............. 279 |
| 80.1 (225/281) | IGKV1-33*01 | ...T.A.T...C.........G..G....C.G..............A... 210 | .A............. 279 |
| 78.0 (213/273) | IGKV1-27*01 | ...TCA.TC............G..G....C.G...G........C... 210 | .A.A...------- 273) |
| 86.8 (33/38) | IGKJ1*01 | ------------------------------------ | ------------- |
| 88.2 (30/34) | IGKJ4*02 | ------------------------------------ | ------------- |
| 77.1 (212/275) | IGKV1D-43*01 | ...CA.TC....C........G..G....C.G..T............C... 210 | .A....T....... 277 |
| 76.5 (212/277) | IGKV1-NL1*01 | ...CA.TC.............G..G....C.G..T............C... 210 | .A....T....... 277 |
| 77.4 (212/274) | A4a | ...TCA.TC............G..G....C.G...G...........C... 211 | .A.A........... 274 |
| 75.8 (210/277) | IGKV1-6*01 | ...TCA.TC............G..G....C.G..T............C... 210 | ......AG...T.C.. 279 |
| 75.8 (210/277) | IGKV1-17*02 | A.TCA.TC.....CA......G..G....C.G..T............C... 210 | ......C..A..... 277 |
| 75.8 (210/277) | IGKV1-16*01 | ...TCA.TC............G..G....C.G..T............C..C 210 | .A....A......... 277 |
| 75.8 (210/277) | IGKV1D-13*01 | ...TCA.TC............G..G....C.G..T............C... 210 | .A....T.A....... 279 |

Figure 8(E)

```
                                 ------->
                     L  W  T  F  G  G  G  T  K  L  E  I  K
ID%          tmpseq_0  307  CTGTGGACGTTCGGTGGAGGCACCAAGCTGGAAATCAAAC  346   (SID 39)
                                                                     L                     (SID 38)
80.1(225/281) IGKV1D-33*01 280  .-.------------------------------------  281   (SID 41)
80.1(225/281) IGKV1-33*01  280  .-.------------------------------------  281   (SID 40)
78.0(213/273) IGKV1-27*01       ---------------------------------------        (SID 42)
86.8(33/38)   IGKJ1*01      1   -------------CCA...G......G............  38    (SID 43)
88.2(30/34)   IGKJ4*02      5   --------------C....G......G.G..........  38    (SID 44)
77.1(212/275) IGKV1D-43*01      ---------------------------------------        (SID 45)
76.5(212/277) IGKV1-NL1*01      ---------------------------------------        (SID 46)
77.4(212/274) A4a               ---------------------------------------        (SID 47)
75.8(210/277) IGKV1-6*01        ---------------------------------------        (SID 48)
75.8(210/277) IGKV1-17*02       ---------------------------------------        (SID 49)
75.8(210/277) IGKV1-16*01       ---------------------------------------        (SID 50)
75.8(210/277) IGKV1D-13*01      ---------------------------------------        (SID 51)
                                                                               (SID 52)
```

Figure 9A

Amino Acid Sequence of Alper-sGMF-BETA mAb Heavy Chain (SEQ ID NO. 1)

VQLQQSGPEL VKPGASVKMS CKASGYTFTS YVMHWVKQKP 40
                                  ---------
                                    cdr1

GQGLEWIGYI NPYNEGTKYN EKFKGKATLT SDKSSSTAYM 80
           -------------------
                  cdr2

ELSSLTSEDS AVYYCARSTM ITTGFAYWGQ GTTVT 115
                     ----------
                        cdr3

CDR1: YTFTSYVMH (SEQ ID NO. 2)
CDR2: YINPYNEGTKYNEKFKG (SEQ ID NO. 3)
CDR3: STM ITTGFAY (SEQ ID NO. 4)

Figure 9B

Amino Acid Sequence of Alper-sGMF-BETA mAb Kappa Chain (SEQ ID NO. 5)

DILMTQSPSS LSASLGGKVT ITCKASQDIN KYIAWYQHKP 40
                              ────────────
                                  cdr1

GEGPRLLIHY TSTLQPGIPS RFSGSGSGRD YSFSITNLEP 80
           ──────────
              cdr2

EDIATYYCLQ YDNLWTFGGG TKLEIK 106
           ─────────
              cdr3

CDR1: KASQDINKYIA (SEQ ID NO. 6)
CDR2: YTSTLQP (SEQ ID NO. 7)
CDR3: CLQYDNLWT (SEQ ID NO. 8)

Figure 9C

Full-length GMF-beta Antigen (SEQ ID NO. 9)

MSESLVVCDV AEDLVEKLRK FRFRKETNNA AIIMKIDKDK RLVVLDEELE GISPDELKDE

LPERQPRFIV YSYKYQHDDG RVSYPLCFIF SSPVGCKPEQ QMMYAGSKNK LVQTAELTKV

FEIRNTEDLT EEWLREKLGF FH

Full-length GMF-beta Antigen without Methionine (SEQ ID NO. 10)

SESLVVCDVA EDLVEKLRKF RFRKETNNAA IIMKIDKDKR LVVLDEELEG ISPDELKDEL

PERQPRFIVY SYKYQHDDGR VSYPLCFIFS SPVGCKPEQQ MMYAGSKNKL VQTAELTKVF

EIRNTEDLTE EWLREKLGFF H

Figure 9D

Processed GMF-beta Antigen (SEQ ID NO. 11)

MSESLVVCDV AEDLVEKLRK FRFRKETNNA AIIMKIDKDK RLVVLDEELE GISPDELKDE

LPERQPRFIV YSYKYQHDDG RVSYPLCFIF SSPVGCKPEQ QMMYAGSKNK LVQTAELTKV

FEIRNTEDLT EEWLREKLGF

Processed GMF-beta Antigen without Methionine (SEQ ID NO. 12)

SESLVVCDVA EDLVEKLRKF RFRKETNNAA IIMKIDKDKR LVVLDEELEG ISPDELKDEL

PERQPRFIVY SYKYQHDDGR VSYPLCFIFS SPVGCKPEQQ MMYAGSKNKL VQTAELTKVF

EIRNTEDLTE EWLREKLGF

Figure 9E

Nucleotide Sequence of Alper-sGMF-BETA mAb Heavy Chain (SEQ ID NO: 13)

NNNNNNNNNNNGCGNTTCGCCCTTTGAGGTGCGGAGGAGTCCACTCTGA
GGTCCAGCTGCAGCAGTCTGGACCTGAGCTGGTAAAGCCTGGGCTTCAG
TGAAGATGTCCTGCAAGGCTTCTGGATACACATTCACTAGCTATGTATG
CACTGGGTGAAGCAGAAGCCTGGACAGGGCCTTGAGTGGATTGGATATAT
TAATCCTTACAATGAAGGAACTAAGTACAATGAGAAGTTCAAAGGCAAGG
CCACACTGACTTCAGAACAAATCCTCAGCACACAGCCTACATGGAGCTCAGC
AGCCTGACCTCTGAGGACTCTGCGGTCTATTATTGTGCAAGATGACTAT
GATTACGACGGGGTTTGCTTACTGGGGACCACGGTCACAAGGG

Nucleotide Sequence of Alper-sGMF-BETA mAb Kappa Chain (SEQ ID NO: 14)

NNNNNNNNNNGNNNACGATTCGCCCTTGACATTCTGATGACCCAGTCTCC
ATCCTCACTGTCTGCATCTGTCATCTCTGGGAGGCAAAGTCACCATCACTTGCAAGG
CAAGCCAAGACATTAACAAGTATATAGCTTGTACCAACACAAGCCTGGA
GAAGGTCCTAGGCTGCTCATACATCTACACATTACACCAGCCAGGCAT
CCCATCAAGGTTCAGTGGAAGTGGGTCTGGGAGAGATTATTCCTTCAGCA
TCACCAACCTGGAACTGGAAGATCTGAAGATATTGCAACTTATTATTGTCTACAGTAT
GATAATCTGTGGACGTTCGGTGGAGGCACCAAGCTGGAAATCAAACGGGC
TGATGCTGCCCAACTGTATCCATCTTCCCAAGGGGCGAATTCGCGGCCGCT

Figure 9F

Amino Acid Sequences of GMF-beta Epitopes

SEQ ID NO: 15:   K.LVQTAELTK.V

SEQ ID NO: 16:   K.ETNNAAIIMK.I

SEQ ID NO: 17:   R.NTEDLTEEWLR.E

SEQUENCE LISTING

<160> NUMBER OF SEQ ID NOS: 52

<210> SEQ ID NO 1
<211> LENGTH: 115
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 1

Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
            20                  25                  30

Met His Trp Val Lys Gln Lys Pro Gly Gln Gly Leu Glu Trp Ile Gly
        35                  40                  45

Tyr Ile Asn Pro Tyr Asn Glu Gly Thr Lys Tyr Asn Glu Lys Phe Lys
    50                  55                  60

Gly Lys Ala Thr Leu Thr Ser Asp Lys Ser Ser Ser Thr Ala Tyr Met
65                  70                  75                  80

Glu Leu Ser Ser Leu Thr Ser Glu Asp Ser Ala Val Tyr Tyr Cys Ala
                85                  90                  95

Arg Ser Thr Met Ile Thr Thr Gly Phe Ala Tyr Trp Gly Gln Gly Thr
            100                 105                 110

Thr Val Thr
        115

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Thr Phe Thr Ser Tyr Val Met His
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ile Asn Pro Tyr Asn Glu Gly Thr Lys Tyr Asn Glu Lys Phe Lys
1               5                   10                  15

Gly

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Thr Met Ile Thr Thr Gly Phe Ala Tyr
1               5                   10

<210> SEQ ID NO 5
<211> LENGTH: 106
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 5

Asp Ile Leu Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Glu Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Thr Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Gln Asp Ile Asn Lys Tyr Ile Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Thr Ser Thr Leu Gln Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Leu Gln Tyr Asp Asn Leu Trp Thr
1               5

<210> SEQ ID NO 9
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Glu Ser Leu Val Val Cys Asp Val Ala Glu Asp Leu Val Glu

```
                 1               5                  10                 15
Lys Leu Arg Lys Phe Arg Phe Arg Lys Glu Thr Asn Asn Ala Ala Ile
                20                 25                 30

Ile Met Lys Ile Asp Lys Asp Lys Arg Leu Val Val Leu Asp Glu Glu
                35                 40                 45

Leu Glu Gly Ile Ser Pro Asp Glu Leu Lys Asp Glu Leu Pro Glu Arg
                50                 55                 60

Gln Pro Arg Phe Ile Val Tyr Ser Tyr Lys Tyr Gln His Asp Asp Gly
65                 70                 75                 80

Arg Val Ser Tyr Pro Leu Cys Phe Ile Phe Ser Ser Pro Val Gly Cys
                85                 90                 95

Lys Pro Glu Gln Gln Met Met Tyr Ala Gly Ser Lys Asn Lys Leu Val
                100                105                110

Gln Thr Ala Glu Leu Thr Lys Val Phe Glu Ile Arg Asn Thr Glu Asp
                115                120                125

Leu Thr Glu Glu Trp Leu Arg Glu Lys Leu Gly Phe Phe His
                130                135                140

<210> SEQ ID NO 10
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Glu Ser Leu Val Val Cys Asp Val Ala Glu Asp Leu Val Glu Lys
1               5                  10                 15

Leu Arg Lys Phe Arg Phe Arg Lys Glu Thr Asn Asn Ala Ala Ile Ile
                20                 25                 30

Met Lys Ile Asp Lys Asp Lys Arg Leu Val Val Leu Asp Glu Glu Leu
                35                 40                 45

Glu Gly Ile Ser Pro Asp Glu Leu Lys Asp Glu Leu Pro Glu Arg Gln
                50                 55                 60

Pro Arg Phe Ile Val Tyr Ser Tyr Lys Tyr Gln His Asp Asp Gly Arg
65                 70                 75                 80

Val Ser Tyr Pro Leu Cys Phe Ile Phe Ser Ser Pro Val Gly Cys Lys
                85                 90                 95

Pro Glu Gln Gln Met Met Tyr Ala Gly Ser Lys Asn Lys Leu Val Gln
                100                105                110

Thr Ala Glu Leu Thr Lys Val Phe Glu Ile Arg Asn Thr Glu Asp Leu
                115                120                125

Thr Glu Glu Trp Leu Arg Glu Lys Leu Gly Phe Phe His
                130                135                140

<210> SEQ ID NO 11
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ser Glu Ser Leu Val Val Cys Asp Val Ala Glu Asp Leu Val Glu
1               5                  10                 15

Lys Leu Arg Lys Phe Arg Phe Arg Lys Glu Thr Asn Asn Ala Ala Ile
                20                 25                 30
```

```
Ile Met Lys Ile Asp Lys Asp Lys Arg Leu Val Val Leu Asp Glu Glu
        35                  40                  45

Leu Glu Gly Ile Ser Pro Asp Glu Leu Lys Asp Glu Leu Pro Glu Arg
    50                  55                  60

Gln Pro Arg Phe Ile Val Tyr Ser Tyr Lys Tyr Gln His Asp Asp Gly
65                  70                  75                  80

Arg Val Ser Tyr Pro Leu Cys Phe Ile Phe Ser Ser Pro Val Gly Cys
                85                  90                  95

Lys Pro Glu Gln Gln Met Met Tyr Ala Gly Ser Lys Asn Lys Leu Val
            100                 105                 110

Gln Thr Ala Glu Leu Thr Lys Val Phe Glu Ile Arg Asn Thr Glu Asp
        115                 120                 125

Leu Thr Glu Glu Trp Leu Arg Glu Lys Leu Gly Phe
    130                 135                 140

<210> SEQ ID NO 12
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Glu Ser Leu Val Val Cys Asp Val Ala Glu Asp Leu Val Glu Lys
1               5                   10                  15

Leu Arg Lys Phe Arg Phe Arg Lys Glu Thr Asn Asn Ala Ala Ile Ile
            20                  25                  30

Met Lys Ile Asp Lys Asp Lys Arg Leu Val Val Leu Asp Glu Glu Leu
        35                  40                  45

Glu Gly Ile Ser Pro Asp Glu Leu Lys Asp Glu Leu Pro Glu Arg Gln
    50                  55                  60

Pro Arg Phe Ile Val Tyr Ser Tyr Lys Tyr Gln His Asp Asp Gly Arg
65                  70                  75                  80

Val Ser Tyr Pro Leu Cys Phe Ile Phe Ser Ser Pro Val Gly Cys Lys
                85                  90                  95

Pro Glu Gln Gln Met Met Tyr Ala Gly Ser Lys Asn Lys Leu Val Gln
            100                 105                 110

Thr Ala Glu Leu Thr Lys Val Phe Glu Ile Arg Asn Thr Glu Asp Leu
        115                 120                 125

Thr Glu Glu Trp Leu Arg Glu Lys Leu Gly Phe
    130                 135

<210> SEQ ID NO 13
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 13
nnnnnnnnnn nngcgnttcg cccctttgagg tgcggaggag tccactctga ggtccagctg     60
```

```
cagcagtctg gacctgagct ggtaaagcct ggggcttcag tgaagatgtc ctgcaaggct      120
tctggataca cattcactag ctatgttatg cactgggtga agcagaagcc tgggcagggc      180
cttgagtgga ttggatatat taatccttac aatgaaggaa ctaagtacaa tgagaagttc      240
aaaggcaagg ccacactgac ttcagacaaa tcctccagca cagcctacat ggagctcagc      300
agcctgacct ctgaggactc tgcggtctat tattgtgcaa gatcgactat gattacgacg      360
gggtttgctt actggggcca aggaccacg gtcacaaggg                             400
```

<210> SEQ ID NO 14
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(10)
<223> OTHER INFORMATION: a, c, t, g, unknown or other
<220> FEATURE:
<221> NAME/KEY: modified_base
<222> LOCATION: (12)..(14)
<223> OTHER INFORMATION: a, c, t, g, unknown or other

<400> SEQUENCE: 14

```
nnnnnnnnnn gnnnacgatt cgcccttgac attctgatga cccagtctcc atcctcactg      60
tctgcatctc tgggaggcaa agtcaccatc acttgcaagg caagccaaga cattaacaag      120
tatatagctt ggtaccaaca caagcctgga gaaggtccta ggctgctcat acattacaca      180
tctacattac agccaggcat cccatcaagg ttcagtggaa gtgggtctgg agagagattat     240 tccttcagca tcaccaacct ggaacctgaa gatattgcaa cttattattg tctacagtat      300
gataatctgt ggacgttcgg tggaggcacc aagctggaaa tcaaacgggc tgatgctgcc      360
caactgtatc catcttccca agggcgaatt cgcggccgct                            400
```

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Leu Val Gln Thr Ala Glu Leu Thr Lys Val
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Glu Thr Asn Asn Ala Ala Ile Ile Met Lys Ile
1               5                   10

<210> SEQ ID NO 17
<211> LENGTH: 13
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 17

Arg Asn Thr Glu Asp Leu Thr Glu Glu Trp Leu Arg Glu
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Thr Met Ile Thr Thr Gly Phe Ala Tyr Trp Gly Gln Gly Thr Thr
1               5                   10                  15

Val Thr

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Trp Thr Phe Gly Gly Gly Thr Lys Leu Glu Ile Lys
1               5                   10

<210> SEQ ID NO 20
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (4)..(347)

<400> SEQUENCE: 20 gag gtc cag ctg cag cag tct gga cct gag ctg gta aag cct ggg gct        48
    Val Gln Leu Gln Gln Ser Gly Pro Glu Leu Val Lys Pro Gly Ala
    1               5                   10                  15 tca gtg aag atg tcc tgc aag gct tct gga tac aca ttc act agc tat        96
Ser Val Lys Met Ser Cys Lys Ala Ser Gly Tyr Thr Phe Thr Ser Tyr
                20                  25                  30 gtt atg cac tgg gtg aag cag aag cct ggg cag ggc ctt gag tgg att       144
Val Met His Trp Val Lys Gln Lys Pro Gly Gln Gly Leu Glu Trp Ile
            35                  40                  45 gga tat att aat cct tac aat gaa gga act aag tac aat gag aag ttc       192
Gly Tyr Ile Asn Pro Tyr Asn Glu Gly Thr Lys Tyr Asn Glu Lys Phe
        50                  55                  60 aaa ggc aag gcc aca ctg act tca gac aaa tcc tcc agc aca gcc tac       240
Lys Gly Lys Ala Thr Leu Thr Ser Asp Lys Ser Ser Ser Thr Ala Tyr
    65                  70                  75 atg gag ctc agc agc ctg acc tct gag gac tct gcg gtc tat tat tgt       288
Met Glu Leu Ser Ser Leu Thr Ser Glu Asp Ser Ala Val Tyr Tyr Cys
80                  85                  90                  95 gca aga tcg act atg att acg acg ggg ttt gct tac tgg ggc caa ggg       336
Ala Arg Ser Thr Met Ile Thr Thr Gly Phe Ala Tyr Trp Gly Gln Gly
                100                 105                 110

```
acc acg gtc ac                                                    347
Thr Thr Val Thr
            115

<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
            20                  25                  30

Met His Trp Val Lys Gln Lys Pro Gly Gln Gly Leu Glu Trp Ile Gly
        35                  40                  45

Tyr Ile Asn Pro Tyr Asn Glu Gly Thr Lys Tyr Asn Glu Lys Phe Lys
    50                  55                  60

Gly Lys Ala Thr Leu Thr Ser Asp Lys Ser Ser Ser Thr Ala Tyr Met
65                  70                  75                  80

Glu Leu Ser Ser Leu Thr Ser Glu Asp Ser Ala Val Tyr Tyr Cys Ala
                85                  90                  95

Arg Ser Thr Met Ile Thr Thr Gly Phe Ala Tyr Trp Gly Gln Gly Thr
            100                 105                 110

Thr Val Thr
        115

<210> SEQ ID NO 22
<211> LENGTH: 293
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3)..(293)

<400> SEQUENCE: 22 ag gtg cag ctg gtg cag tct ggg gct gag gtg aag aag cct ggg gcc     47
   Val Gln Leu Val Gln Ser Gly Ala Glu Val Lys Lys Pro Gly Ala
   1               5                   10                  15 tca gtg aag gtc tcc tgc aag gct tct gga tac acc ttc acc ggc tac    95
Ser Val Lys Val Ser Cys Lys Ala Ser Gly Tyr Thr Phe Thr Gly Tyr
                20                  25                  30 tat atg cac tgg gtg cga cag gcc cct gga caa ggg ctt gag tgg atg   143
Tyr Met His Trp Val Arg Gln Ala Pro Gly Gln Gly Leu Glu Trp Met
            35                  40                  45 gga tgg atc aac cct aac agt ggt ggc aca aac tat gca cag aag ttt   191
Gly Trp Ile Asn Pro Asn Ser Gly Gly Thr Asn Tyr Ala Gln Lys Phe
        50                  55                  60 cag ggc agg gtc acc atg acc agg gac acg tcc atc agc aca gcc tac   239
Gln Gly Arg Val Thr Met Thr Arg Asp Thr Ser Ile Ser Thr Ala Tyr
    65                  70                  75 atg gag ctg agc agg ctg aga tct gac gac acg gcc gtg tat tac tgt   287
Met Glu Leu Ser Arg Leu Arg Ser Asp Asp Thr Ala Val Tyr Tyr Cys
80                  85                  90                  95 gcg aga                                                           293
Ala Arg
```

<210> SEQ ID NO 23
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Val Gln Leu Val Gln Ser Gly Ala Glu Val Lys Lys Pro Gly Ala Ser
1               5                   10                  15

Val Lys Val Ser Cys Lys Ala Ser Gly Tyr Thr Phe Thr Gly Tyr Tyr
            20                  25                  30

Met His Trp Val Arg Gln Ala Pro Gly Gln Gly Leu Glu Trp Met Gly
        35                  40                  45

Trp Ile Asn Pro Asn Ser Gly Gly Thr Asn Tyr Ala Gln Lys Phe Gln
    50                  55                  60

Gly Arg Val Thr Met Thr Arg Asp Thr Ser Ile Ser Thr Ala Tyr Met
65                  70                  75                  80

Glu Leu Ser Arg Leu Arg Ser Asp Asp Thr Ala Val Tyr Tyr Cys Ala
                85                  90                  95

Arg

<210> SEQ ID NO 24
<211> LENGTH: 293
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (112)..(112)
<223> OTHER INFORMATION: a, c, t, g, unknown or other

<400> SEQUENCE: 24
aggtgcagct ggtgcagtct ggggctgagg tgaagaagct tggggcctca gtgaaggtct      60
cctgcaaggc ttctggatac accttcaccg gctactatat gcactgggtg cnacaggccc    120
ctggacaagg gcttgagtgg atgggatgga tcaaccctaa cagtggtggc acaaactatg    180
cacagaagtt tcagggcagg gtcaccatga ccagggacac gtccatcagc acagcctaca    240
tggagctgag caggctgaga tctgacgaca cggccgtgta ttactgtgcg aga           293

<210> SEQ ID NO 25
<211> LENGTH: 293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
aggtgcagct ggtgcagtct ggggctgagg tgaagaagcc tggggcctca gtgaaggtct      60
cctgcaaggc ttctggatac accttcaccg gctactatat gcactgggtg cgacaggccc    120
ctggacaagg gcttgagtgg atgggatgga tcaaccctaa cagtggtggc acaaactatg    180
cacagaagtt tcagggctgg gtcaccatga ccagggacac gtccatcagc acagcctaca    240
tggagctgag caggctgaga tctgacgaca cggccgtgta ttactgtgcg aga           293

<210> SEQ ID NO 26
<211> LENGTH: 10

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tatgattacg                                                               10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tatgattacg                                                               10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctaactgggg                                                               10

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctggggccaa gggaccacgg tcac                                               24

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tttgactact ggggccaagg gaccctggtc ac                                      32

<210> SEQ ID NO 31
<211> LENGTH: 293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
aggttcagct ggtgcagtct ggagctgagg tgaagaagcc tggggcctca gtgaaggtct        60
cctgcaaggc ttctggttac acctttacca gctatggtat cagctgggtg cgacaggccc       120
ctggacaagg gcttgagtgg atgggatgga tcagcgctta caatggtaac acaaactatg       180
cacagaagct ccagggcaga gtcaccatga ccacagacac atccacgagc acagcctaca       240
```
tggagctgag gagcctgaga tctgacgaca cggccgtgta ttactgtgcg aga        293

<210> SEQ ID NO 32
<211> LENGTH: 293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
aggtccagct tgtgcagtct ggggctgagg tgaagaagcc tggggcctca gtgaaggttt        60
cctgcaaggc ttctggatac accttcacta gctatgctat gcattgggtg cgccaggccc       120
ccggacaaag gcttgagtgg atgggatgga tcaacgctgg caatggtaac acaaaatatt       180
cacagaagtt ccagggcaga gtcaccatta ccagggacac atccgcgagc acagcctaca       240
tggagctgag cagcctgaga tctgaagaca cggctgtgta ttactgtgcg aga             293

<210> SEQ ID NO 33
<211> LENGTH: 293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
aggttcagct ggtgcagtct ggggctgagg tgaagaagcc tggggcctca gtgaaggttt        60
cctgcaaggc ttctggatac accttcacta gctatgctat gcattgggtg cgccaggccc       120
ccggacaaag gcttgagtgg atgggatgga gcaacgctgg caatggtaac acaaaatatt       180
cacaggagtt ccagggcaga gtcaccatta ccagggacac atccgcgagc acagcctaca       240
tggagctgag cagcctgaga tctgaggaca tggctgtgta ttactgtgcg aga             293

<210> SEQ ID NO 34
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gaggtccagc tggtacagtc tggggctgag gtgaagaagc tggggctac agtgaaaatc        60 tcctgcaagg tttctggata caccttcacc gactactaca tgcactgggt gcaacaggcc       120
cctggaaaag ggcttgagtg gatgggactt gttgatcctg aagatggtga aacaatatac       180
gcagagaagt tccagggcag agtcaccata accgcggaca cgtctacaga cacagcctac       240
atggagctga gcagcctgag atctgaggac acggccgtgt attactgtgc aa              292

<210> SEQ ID NO 35
<211> LENGTH: 293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
aggtccagct ggtgcagtct ggggctgagg tgaagaagcc tggtcctca gtgaaggtct        60 cctgcaaggc ttctggaggc accttcagca gctatgctat cagctgggtg cgacaggccc       120

```
ctggacaagg gcttgagtgg atgggaggga tcatccctat ccttggtata gcaaactacg      180
cacagaagtt ccagggcaga gtcacgatta ccgcggacaa atccacgagc acagcctaca      240
tggagctgag cagcctgaga tctgaggaca cggccgtgta ttactgtgcg aga             293
```

<210> SEQ ID NO 36
<211> LENGTH: 293
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
aggtgcagct ggtgcagtct ggggctgagg tgaagaagcc tggggcctca gtgaaggttt      60
cctgcaaggc atctggatac accttcacca gctactatat gcactgggtg cgacaggccc     120
ctggacaagg gcttgagtgg atgggaataa tcaaccctag tggtggtagc acaagctacg     180
cacagaagtt ccagggcaga gtcaccatga ccagggacac gtccacgagc acagtctaca     240
tggagctgag cagcctgaga tctgaggaca cggccgtgta ttactgtgct aga             293
```

<210> SEQ ID NO 37
<211> LENGTH: 293
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
aggtgcagct ggtgcagtct ggggctgagg tgaagaagcc tggggcctca gtgaaggttt      60
cctgcaaggc atctggatac accttcacca gctactatat gcactgggtg cgacaggccc     120
ctggacaagg gcttgagtgg atgggaataa tcaaccctag tggtggtagc acaagctacg     180
cacagaagtt ccagggcaga gtcaccatga ccagggacac gtccacgagc acagtctaca     240
tggagctgag cagcctgaga tctgaggaca cggccgtgta ttactgtgcg aga             293
```

<210> SEQ ID NO 38
<211> LENGTH: 319
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(318)

<400> SEQUENCE: 38

```
gac att ctg atg acc cag tct cca tcc tca ctg tct gca tct ctg gga       48
Asp Ile Leu Met Thr Gln Ser Pro Ser Ser Leu Ser Ala Ser Leu Gly
1               5                   10                  15 ggc aaa gtc acc atc act tgc aag gca agc caa gac att aac aag tat       96
Gly Lys Val Thr Ile Thr Cys Lys Ala Ser Gln Asp Ile Asn Lys Tyr
            20                  25                  30 ata gct tgg tac caa cac aag cct gga gaa ggt cct agg ctg ctc ata      144
Ile Ala Trp Tyr Gln His Lys Pro Gly Glu Gly Pro Arg Leu Leu Ile
        35                  40                  45 cat tac aca tct aca tta cag cca ggc atc cca tca agg ttc agt gga      192
His Tyr Thr Ser Thr Leu Gln Pro Gly Ile Pro Ser Arg Phe Ser Gly
    50                  55                  60 agt ggg tct ggg aga gat tat tcc ttc agc atc acc aac ctg gaa cct      240
```

```
Ser Gly Ser Gly Arg Asp Tyr Ser Phe Ser Ile Thr Asn Leu Glu Pro
 65                  70                  75                  80 gaa gat att gca act tat tat tgt cta cag tat gat aat ctg tgg acg        288
Glu Asp Ile Ala Thr Tyr Tyr Cys Leu Gln Tyr Asp Asn Leu Trp Thr
                 85                  90                  95 ttc ggt gga ggc acc aag ctg gaa atc aaa c                              319
Phe Gly Gly Gly Thr Lys Leu Glu Ile Lys
                100                 105

<210> SEQ ID NO 39
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Leu Met Thr Gln Ser Pro Ser Ser Leu Ser Ala Ser Leu Gly
1               5                  10                  15

Gly Lys Val Thr Ile Thr Cys Lys Ala Ser Gln Asp Ile Asn Lys Tyr
                20                  25                  30

Ile Ala Trp Tyr Gln His Lys Pro Gly Glu Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Thr Asn Leu Glu Pro
 65                  70                  75                  80

Glu Asp Ile Ala Thr Tyr Tyr Cys Leu Gln Tyr Asp Asn Leu Trp Thr
                 85                  90                  95

Phe Gly Gly Gly Thr Lys Leu Glu Ile Lys
                100                 105

<210> SEQ ID NO 40
<211> LENGTH: 281
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(281)

<400> SEQUENCE: 40 gac atc cag atg acc cag tct cca tcc tcc ctg tct gca tct gta gga         48
Asp Ile Gln Met Thr Gln Ser Pro Ser Ser Leu Ser Ala Ser Val Gly
1               5                  10                  15 gac aga gtc acc atc act tgc cag gcg agt cag gac att agc aac tat         96
Asp Arg Val Thr Ile Thr Cys Gln Ala Ser Gln Asp Ile Ser Asn Tyr
                20                  25                  30 tta aat tgg tat cag cag aaa cca ggg aaa gcc cct aag ctc ctg atc        144
Leu Asn Trp Tyr Gln Gln Lys Pro Gly Lys Ala Pro Lys Leu Leu Ile
            35                  40                  45 tac gat gca tcc aat ttg gaa aca ggg gtc cca tca agg ttc agt gga        192
Tyr Asp Ala Ser Asn Leu Glu Thr Gly Val Pro Ser Arg Phe Ser Gly
        50                  55                  60 agt gga tct ggg aca gat ttt act ttc acc atc agc agc ctg cag cct        240
Ser Gly Ser Gly Thr Asp Phe Thr Phe Thr Ile Ser Ser Leu Gln Pro
 65                  70                  75                  80 gaa gat att gca aca tat tac tgt caa cag tat gat aat ct                 281
Glu Asp Ile Ala Thr Tyr Tyr Cys Gln Gln Tyr Asp Asn Leu
                 85                  90
```

<210> SEQ ID NO 41
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu
                85                  90

<210> SEQ ID NO 42
<211> LENGTH: 281
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg aagtggatc tgggacagat tttactttca ccatcagcag cctgcagcct    240
gaagatattg caacatatta ctgtcaacag tatgataatc t                       281

<210> SEQ ID NO 43
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tat                                273

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtggacgttc ggccaaggga ccaaggtgga aatcaaac                                    38

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
acgttcggcg gagggaccaa ggtggagatc aaac                                        34

<210> SEQ ID NO 46
<211> LENGTH: 275
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
catccggatg acccagtctc cattctccct gtctgcatct gtaggagaca gagtcaccat            60
cacttgctgg gccagtcagg gcattagcag ttatttagcc tggtatcagc aaaaaccagc           120
aaaagcccct aagctcttca tctattatgc atccagtttg caaagtgggg tcccatcaag           180
gttcagcggc agtggatctg ggacggatta cactctcacc atcagcagcc tgcagcctga           240
agattttgca acttattact gtcaacagta ttata                                      275

<210> SEQ ID NO 47
<211> LENGTH: 277
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gacatccaga tgacccagtc tccatcctcc ctgtctgcat ctgtaggaga cagagtcacc            60
atcacttgcc gggcgagtca gggcattagc aattctttag cctggtatca gcagaaacca           120
gggaaagccc ctaagctcct gctctatgct gcatccagat ggaaagtggg gtcccatcc            180 aggttcagtg gcagtggatc tgggacggat tacactctca ccatcagcag cctgcagcct           240
gaagattttg caacttatta ctgtcaacag tattata                                    277

<210> SEQ ID NO 48
<211> LENGTH: 274
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gacatccaga tgacccagtc tccatcctcc ctgtctgcat ctgtaggaga cagagtcacc            60
atcacttgcc gggcgagtca gggcattagc aattatttag cctggtatca gcagaaacca           120
gggaaagttc ctaagctcct gatctatgct gcatccgctt tgcaatcagg gggtcccatc           180
tcggttcagt ggcagtggat ctgggacaga tttcactctc accatcagca gcctgcagcc           240
tgaagatgtt gcaacttatt actgtcaaaa gtat                                       274

<210> SEQ ID NO 49
<211> LENGTH: 277
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
catccagatg acccagtctc catcctccct gtctgcatct gtaggagaca gagtcaccat    60
cacttgccgg gcaagtcagg gcattagaaa tgatttaggc tggtatcagc agaaaccagg    120
gaaagcccct aagctcctga tctatgctgc atccagttta caaagtgggg tcccatcaag    180
gttcagcggc agtggatctg gcacagattt cactctcacc atcagcagcc tgcagcctga    240
agattttgca acttattact gtctacaaga ttacaat                             277

<210> SEQ ID NO 50
<211> LENGTH: 277
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gacatccaga tgacccagtc tccatcctcc ctgtctgcat ctgtaggaga cagagtcacc    60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcaa cctgcagcct    240
gaagattttg caacttatta ctgtctacag cataata                             277

<210> SEQ ID NO 51
<211> LENGTH: 277
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gacatccaga tgacccagtc tccatcctca ctgtctgcat ctgtaggaga cagagtcacc    60
atcacttgtc gggcgagtca gggcattagc aattatttag cctggtttca gcagaaacca    120
gggaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataata                             277

<210> SEQ ID NO 52
<211> LENGTH: 277
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
catccagttg acccagtctc catcctccct gtctgcatct gtaggagaca gagtcaccat    60
cacttgccgg gcaagtcagg gcattagcag tgctttagcc tggtatcagc agaaaccagg    120
gaaagctcct aagctcctga tctatgatgc ctccagtttg gaaagtgggg tcccatcaag    180

```
gttcagcggc agtggatctg ggacagattt cactctcacc atcagcagcc tgcagcctga    240
agattttgca acttattact gtcaacagtt taataat                             277
```

MONOCLONAL ANTIBODIES AGAINST GMF-B ANTIGENS, AND USES THEREFOR

RELATED DISCLOSURES

The present application claims the benefit of U.S. Provisional Application No. 61/260,716, filed Nov. 12, 2009, the contents of which are herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Nov. 11, 2010, is named 23440012.txt and is 35,267 bytes in size.

FIELD OF THE DISCLOSURE

The present disclosure generally relates to monoclonal antibodies (mAbs), hybridoma lines that secrete antibodies or fragments thereof, and the use of antibodies and antibody fragments to preferentially detect antigens.

BACKGROUND OF THE DISCLOSURE

Dementia is a debilitating and life-altering disease that leads to memory impairment and decline of normal executive functioning. While the causes of dementia are numerous, the leading causes among patients 60 years and older are Alzheimer's disease (AD) and dementia with Lewy bodies. AD represents a significant public health concern because of its associated personal, social and economic burdens. Previously, diagnosis of AD required histopathological confirmation based on lesions in brain cortical structures, which lesions are characterized by an extracellular senile plaque and an intracellular neurofibrillary tangle. Such histopathological confirmation poses unique challenges due to the sensitivity of brain tissue to biopsy. As such, better diagnostic tools for identifying AD are desirable.

GMF-B (glia maturation factor beta) belongs to the actin-binding proteins (ADF) structural family. GMF-B is a 141 amino acid protein isolated from brain and identified as a growth and differentiation factor, acting on neuorons as well as glia. GMF-B is expressed predominantly in the brain, especially by astrocytes an some neuronal cells. GMF-B is located on chromosome 14q22.2. GMF-B has been sequenced and otherwise characterized under UniProt P60983, NCBI Gene 2764; NCBI RefSeq NP_004115.1; NCBI RefSeq NM_004124.2, NP_006187; NCBI UniGene 5093; and NCBI Accession AK130439, AAA91317. Homologues of GMF-B are also known, including, but not limited to, homologues of GMF-B in the mouse (see NCBI UniGene 23983; UniProt P60335; and NCBI RefSeq NM_011865, NP_035995), dog, and rat, and GMF-B is highly conserved.

GMF-B is an acidic (pI=5.2) protein of 17 kDa. The unprocessed bovine and human GMF-B having a length of 142 amino acids, including the first methionine, and contain three cysteine residues (Lim et al., *FASEB J* 4:3360-3363, 1990; Kaplan et al., *Journal of Neurochemistry* 57(2):483-490, 1991). See SEQ ID NO: 9. Two of the cysteines (position 87 and 96 of unprocessed GMF-B (SEQ ID NO: 9); position 87 and 96 of processed GMF-B (SEQ ID NO: 11); and position 86 and 95 of Met processed GMF-B (SEQ ID NO: 10 or 12)) form a disulfide bond that is reported as essential for bioactivity. GMF-B may also be phosphorylated at residue 84 of SEQ ID NOs: 9 or 11 or residue 83 of SEQ ID NO: 10 or 12. GMF-B has a blocked amino terminus (N-Acetyl-serine). Cell surface expression of GMF-B has been shown, and it was documented that GMF-B is not secreted (Lim et al., FASEB J, 4:3360-3363, 1990). GMF-B does not display any significant homology to other sequenced proteins (Lim and Zaheer, 1991). For a related highly homologous factor see also: GMF-gamma.

GMF-B is reported to play a role in the differentiation, maintenance and regeneration of the nervous system. GMF-B also has been reported to support the progression of certain auto-immune diseases, possibly through its ability to induce the production and secretion of various pro-inflammatory cytokines e.g., interleukin-1beta and MHC class II. Moreover, the addition of a soluble recombinant GMF-B to neoplastic cells in culture resulted in a reported inhibition of proliferation and the arresting of cells in the G0/G1 phase (Lim et al., *Cell Regulation* 1:741-746, 1990) (Lim et al., *J Biol. Chem.* 271:22953-56, 1996). Furthermore, GMF-B was reported to inhibit the proliferation of tumors derived from neuronal cell types. Unlimited growth of gliomas has been reported to be due to a defect in the transport of GMF-B from the cytosol to the cell surface. A reversible inhibition of a number of neuronal and non-neuronal neoplastic cells by GMF-B is also observed (Lim et al, 1990).

Many reports also suggest that GMF-B plays a role in neuroprotection against adverse environmental conditions (Zaheer, et al., *Neurochem. Res.* 26: 1293-1299, 2001; Lim, et al., *Neurochem. Res.* 23: 1445-1451, 1998; Lim, et al., *J. Neurochem.* 74: 596-602, 2000; Zaheer, et al., *Neurosci. Lett.* 265: 203-206, 1999; Pantazis et al., *Brain Res.* 865: 59-76, 2000). For example, the application of GMF-B to an injured brain promotes the appearance of large neurons in the cerebral cortex (Kaplan, et al., *J. Neuorchem.* 57: 483-490, 1991); Lim, et al., *Proc. Natl. Acad. Sci. USA* 86: 3901-3905, 1989; Lim, et al., *Methods Enzymol.* 147: 225-235, 1987; Lim, et al., *Brain Res.* 430: 93-100, 1987; Lim, et al., *Brain Res.* 468: 277-284, 1988; Lim, et al., *Brain Res.* 504: 154-158, 1989; Bosch, et al., *J. Neurosci.* 9: 3690-3698, 1989; Nieto-Sampedro, et al., *Neurosci. Lett.* 86:361-365, 1988; Lim, et al., *Brain Res.* 430: 49-57, 1987; Ryken, et al., *Int. J. Dev. Neurosci.* 5: 215-225, 1987; Lim, et al., *Cancer Res.* 46: 5241-5247, 1986; Yamazaki, et al., *Histopathology* 47: 292-302, 2005). By contrast, overexpression of GMF-B in astrocytes leads to the destruction of primary oligodendrocytes, implicating a GMF-B-related neural cytotoxicity (Menon, et al., *Neurosci. Res.* 58: 156-163, 2007); Zaheer, et al., *J. Neurochem.* 101: 364-376, 2007; Zaheer, et al., *Neurochem. Res.* 32: 39-47, 2007; Zaheer, et al., *Brain Res.* 1144: 239-247, 2007; Zaheer, et al., *Neurochem. Res.* 32: 2123-2131, 2007).

As such, it there is a need to further examine GMF-B expression in the brain and blood after neural degeneration, such as that caused by dementia, including Alzheimer's disease. For example, of great interest would be the development of additional diagnostic and therapeutic tools for disease states, including for example dementia, based upon GMF-B expression and the use of GMF-B antibodies.

SUMMARY OF THE DISCLOSURE

In one aspect, the present disclosure provides an antibody capable of binding to a soluble and cellular form of GMF-B. In other aspects, the present disclosure provides an antibody capable of binding to a secreted and cellular form of GMF-B. In certain embodiments the antibody may preferentially bind to a soluble form of GMF-B, e.g., with a specific affinity of between $10^{-8}$M and $10^{-11}$M. In other embodiments, the antibody may preferentially bind to a secreted form of GMF-B, e.g., with a specific affinity of between $10^{-8}$M and $10^{-11}$M.

In yet other aspects, the present disclosure provides an antibody capable of selectively reducing the activity of a soluble GMF-B, e.g., in a sample or cell. In yet other aspects, the present disclosure provides an antibody capable of selectively reducing the activity of a secreted GMF-B, e.g., in a sample or a cell.

In yet other aspects, the present disclosure provides an antibody capable of binding to a soluble form of a GMF-B antigen. In certain embodiments, the antibody may preferentially bind to a soluble form of a GMF-B antigen. In yet other embodiments, the preferential binding is relative to a nuclear form of GMF-B. In yet other aspects, the present disclosure provides an antibody capable of preferentially binding to a secreted form of GMF-B antigen.

In yet other aspects, the present disclosure provides an antibody capable of recognizing an epitope selected from the group consisting of SEQ. ID. NO.: 15, SEQ. ID. NO.: 16 and SEQ. ID. NO.: 17.

In yet other aspects, the present disclosure provides an antibody specific for a GMF-B antigen, comprising one or more of the heavy chain CDR antigen binding site sequences set forth in FIG. 7, and one or more of the light chain CDR antigen binding site sequences set forth in FIG. 8. In one embodiment, the antibody specific for a GMF-B antigen comprises the heavy chain CDR antigen binding site sequences CDR1, CDR2, and CDR3 as set forth in FIG. 7, and the light chain CDR antigen binding site sequences CDR1, CDR2, and CDR3 as set forth in FIG. 8.

In yet other aspects, the present disclosure provides an isolated DNA sequence which encodes the heavy chain of an antibody molecule, where the antibody molecule has specificity for GMF-B and where the variable domain of said heavy chain comprises a CDR having the antigen binding site sequences CDR1, CDR2, and CDR3 set forth in FIG. 7.

In yet other aspects, the present disclosure provides an isolated DNA sequence which encodes the light chain of an antibody molecule, where the antibody molecule has specificity for GMF-B and further where the variable domain of the light chain comprises a CDR having the antigen binding site sequences CDR1, CDR2, and CDR3 set forth in FIG. 8.

In yet other aspects, the present disclosure provides a method of determining the status of a cell in a sample by (a) obtaining said sample; (b) contacting said sample with an antibody capable of preferentially detecting a soluble form of GMF-B antigen; and (c) determining quantity or localization of said antigen.

In yet other aspects, the present disclosure provides an immunoassay for detecting a GMF-B antigen which binds to a monoclonal antibody described herein, comprising: (a) contacting the sample with an effective binding amount of an antibody described herein; and (b) detecting the antigen by detecting the binding of the antibody to the GMF-B antigen.

In yet other aspects, the present disclosure provides a method for developing drugs useful in treating and/or diagnosing diseases characterized by the expression of gene products of GMF-B and homologues thereof, comprising the steps of: identifying gene products expressed by GMF-B and homologues thereof in a subject having a disease, and utilizing the gene products as biomarkers in the development and identification of drugs selected from the group consisting of GMF-B antibodies and antibody fragments, inhibiting peptides, siRNA, antisense oligonucleotides, vaccines, and chemical compounds, which specifically target the gene products.

In yet other aspects, the present disclosure provides a method of determining the status of a cell in a sample comprising: (a) obtaining a sample from a subject; (b) contacting the sample with an antibody capable of preferentially detecting a soluble form of GMF-B antigen; and (c) determining the quantity of the antigen.

In yet other aspects, the present disclosure provides a method of determining the status of a cell in a sample comprising: (a) obtaining a sample from a subject; (b) contacting the sample with an antibody capable of preferentially detecting a soluble form of GMF-B antigen; and (c) determining the localization of the antigen.

In yet other aspects, the present disclosure provides a method of determining the status of a cell in a sample comprising: (a) obtaining a sample from a subject; (b) contacting the sample with an antibody capable of preferentially detecting a secreted form of GMF-B antigen; and (c) determining the quantity of the antigen.

In yet other aspects, the present disclosure provides a method of determining the status of a cell in a sample comprising: (a) obtaining a sample from a subject; (b) contacting the sample with an antibody capable of preferentially detecting a secreted form of GMF-B antigen; and (c) determining the localization of the antigen.

In yet other aspects, the present disclosure provides a method of determining the status of a cell in a sample comprising: (a) obtaining a sample; (b) contacting the sample with an antibody capable of preferentially detecting a secreted form of GMF-B antigen; and (c) determining the quantity or localization of the antigen.

Additional objects, advantages and novel features of this invention will be set forth in part in the description that follows, and in part will become apparent to those skilled in the art upon examination of the following description, or may be learned by practicing the invention.

BRIEF DESCRIPTION OF THE DRAWINGS

FIG. 7 also discloses SEQ ID NOS 20, 23, 22, and 24-37, respectively, in order of appearance.

FIG. 8A-8E. Alper-sGMF-B mAb light chain sequence information. FWRs and CDRs of the light chain of a Alper-sGMF-B mAb, in which the polypeptide sequence provided in the top line (SEQ ID NO: 39) corresponds to the sequence of the Alper-sGMF-B mAb. Amino acid residues are numbered using the convention of Kabat et al. Bold residues set forth in underlined text indicate the specificity determining residues (SDRs). FIG. 8 also discloses SEQ ID NOS 38, 41, 40, and 42-52, respectively, in order of appearance.

FIG. 9. Sequence Listing. FIG. 9A shows the amino acid sequences of Alper-sGMF-B mAb heavy chain (SEQ ID NO: 1) and the heavy chain CDR1, CDR2 and CDR3 (SEQ ID NOs: 2, 3 and 4, respectively). FIG. 9B shows the amino acid sequences of Alper-sGMF-B mAb light chain (SEQ ID NO: 5) and the light chain CDR1, CDR2 and CDR3 (SEQ ID NOs: 6, 7 and 8, respectively). FIG. 9C shows the amino acid sequences of the full-length GMF-B antigen (SEQ ID NO: 9) and the full-length GMF-B antigen without methionine (SEQ ID NO: 10). FIG. 9D shows the amino acid sequences of the processed GMF-B antigen (SEQ ID NO: 11) and the processed GMF-B antigen without methionine (SEQ ID NO: 12). FIG. 9E shows the nucleotide sequences of the Alper-sGMF-B mAb heavy chain (SEQ ID NO: 13) and the Alper-sGMF-B mAb light chain (SEQ ID NO: 14). FIG. 9F shows the amino acid sequences of the GMF-B antigen epitopes (SEQ ID NOs: 15, 16 and 17, respectively).

BRIEF DESCRIPTION OF CERTAIN SEQUENCES

Figure 1:
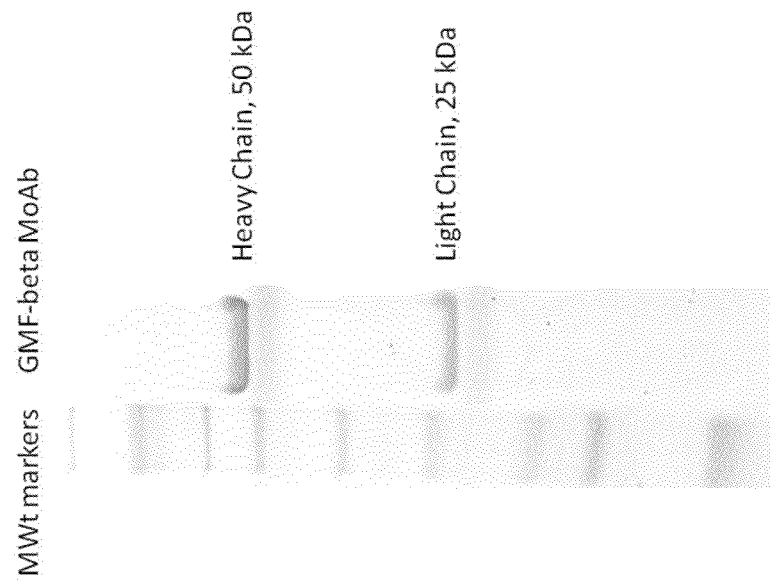
FIG. 1. Coomassie blue staining analysis for purified mAb

SEQ ID NOs: 1 and 21 show the amino acid sequence of Alper-sGMF-B mAb Heavy Chain (see FIG. 7)
SEQ ID NO: 2 shows CDR1 of Alper-sGMF-B mAb Heavy Chain
SEQ ID NO: 3 shows CDR2 of Alper-sGMF-B mAb Heavy Chain
SEQ ID NO: 4 shows CDR3 of Alper-sGMF-B mAb Heavy Chain
SEQ ID NOs: 5 and 39 show the amino acid sequence of Alper-sGMF-B mAb Kappa Chain (see FIG. 8)
SEQ ID NO: 6 shows CDR1 of Alper-sGMF-B mAb Kappa Chain
SEQ ID NO: 7 shows CDR2 of Alper-sGMF-B mAb Kappa Chain
SEQ ID NO: 8 shows CDR3 of Alper-sGMF-B mAb Kappa Chain
SEQ ID NO: 9 shows Full-length GMF-B Antigen
SEQ ID NO: 10 shows Full-length GMF-B Antigen without Methionine
SEQ ID NO: 11 shows Processed GMF-B Antigen
SEQ ID NO: 12 shows Processed GMF-B Antigen without Methionine
SEQ ID NOs: 13 and 20 show the nucleotide sequence of Alper-sGMF-B mAb Heavy Chain (see FIG. 7)
SEQ ID NOs: 14 and 38 shows the nucleotide sequence of Alper-sGMF-B mAb Kappa Chain (see FIG. 8)
SEQ ID NO: 15 shows the amino acid sequence of Epitope 1 of GMF-B
SEQ ID NO: 16 shows the amino acid sequence of Epitope 2 of GMF-B
SEQ ID NO: 17 shows the amino acid sequence of Epitope 3 of GMF-B

DETAILED DESCRIPTION

1. Definitions

Antibody: This refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

Monoclonal Antibody: This refers to antibodies that are identical because they are produced by one type of immune cell that are all clones of a single parent cell. The monoclonal antibodies of the present invention can include intact monoclonal antibodies, antibody fragments, conjugates, or fusion proteins, which contain a $V_H$ and a $V_L$ where the CDRs form the antigen binding site.

Chimeric Antibody: This refers to an antibody which includes sequences derived from two different antibodies, which typically are of different species. Most typically, chimeric antibodies include human and non-human antibody fragments, generally human constant and non-human variable regions. Humanized antibodies can or can not be considered chimeric.

Humanized Antibody: This refers to an antibody derived from a non-human antibody. The humanized antibody retains or substantially retains the antigen-binding properties of the parent antibody but is less immunogenic in humans than its parent antibody.

Antibody Conjugates, Fusion Proteins, and Bispecific Antibodies: These refer to monoclonal antibodies conjugated by chemical methods with radionuclides, drugs, macromolecules, or other agents.

Antigen: This refers to one or more molecules or one or more portions of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly preferential manner, with its corresponding antibody and not with the multitude of other antibodies which can be evoked by other antigens. The binding of antigen to antibody must be above background levels.

Epitope: This refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

Complementarity Determining Region, or CDR: This refers to amino acid sequences which together define the binding affinity and specificity of the natural Fv region of a native immunoglobulin binding site. The light and heavy chains of an immunoglobulin each have three CDRs. By definition, the CDRs of the light chain are bounded by the residues at positions 24 and 34 (CDR1), 50 and 56 (CDR2), 88 and 94 (CDR3); the CDRs of the heavy chain are bounded by the residues at positions 36 and 44 (CDR1), 49-65 (CDR2), and 108-117 (CDR3), using the numbering convention delineated by Kabat et al., (1991) Sequences of Proteins of Immunological Interest, 5th Edition, Department of Health and Human Services, Public Health Service, National Institutes of Health, Bethesda (NIH Publication No. 91-3242).

Framework Region or FWR: This refers to amino acid sequences interposed between CDRs. These portions of the antibody serve to hold the CDRs in an appropriate orientation for antigen binding.

Specificity Determining Residue, or SDR: This refers to amino acid residues that can be unique to Alper-sGMF-B mAb when compared to other IgGs. Preferentially, the SDR is the part of an immunoglobulin that is directly involved in antigen contact.

Constant Region: This refers to the portion of an antibody molecule which confers effector functions. A heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. A light chain constant region can be of the kappa or lambda type, preferably the kappa type.

Immunogenicity: A measure of the ability of a targeting protein or therapeutic moiety to elicit an immune response (humoral or cellular) when administered to a recipient. The present invention is concerned with the immunogenicity of antibodies to GMF-B.

Immunoreactivity: A measure of the ability of an immunoglobulin to recognize and bind to a specific antigen.

GMF-B Antibodies or GMF-B mAbs: This refers to antibodies preferential to expression products of the GMF-B gene and homologues of the GMF-B gene, which can include antibodies specific to modified forms of the expression product that are produced by cancer cells. The antibodies include variants, such as chimeric, humanized, and other variants known to those skilled in the art. GMF-B antibodies are said to be specific for the GMF-B antigen if they exhibit preferential binding to a GMF-B antigen at least 85% of the time, at least 90% of the time, or, in a preferred aspect, at least 95% of the time relative to any other protein.

GMF-B Antigens: This refers to expression products generated by GMF-B, which can be used as antigens, target molecules, biomarkers, or any combination thereof. A GMF-B antigen can be produced by the GMF-B gene and homologues of the GMF-B gene, and can include various modifications introduced by the cells expressing a GMF-B antigen, such as cancer cells.

Substantially Similar Binding Properties: This refers to a chimeric antibody, such as a humanized antibody or fragments thereof which retain the ability to preferentially bind an antigen recognized by the parent antibody used to produce the chimeric antibody, such as a humanized antibody, or fragments thereof. Preferably, the affinity of a chimeric antibody, humanized antibody, or antibody fragment is at least about 10% of the affinity of the parent antibody, more preferably at least about 25%, even more preferably at least about 50%. Most preferably, a chimeric antibody, preferably a humanized antibody, or antibody fragments thereof exhibit an antigen-binding affinity that is at least about 75% of the affinity of the parent antibody. Methods for assaying antigen-binding affinity are known in the art and include half-maximal binding assays, competition assays, and Scatchard analysis. In a preferred aspect, antigen-binding affinity is assayed using a competition assay.

Substantially Homologous: Refers to immunoglobulin sequences that exhibit at least about 85% identity, more preferably about 90% identity, most preferably about 95% identity with a reference immunoglobulin sequence, where % identity is determined by comparing the number identical of amino acid residues between the two immunoglobulins, where the positions of the amino acid residues are indicated using the Kabat numbering scheme.

Sameness for Monoclonal Antibody Products: For the purpose of determining sameness of monoclonal antibodies, and products thereof, the complementarity determining regions of the heavy and light chain variable regions are the principal molecular structural feature of a monoclonal antibody product. Two monoclonal antibodies can be considered the same if the amino acid sequences of the CDRs were the same, or if there were only minor amino acid differences between them. Whether differences in the amino acid sequences are minor can be determined by factors that include (but are not limited to) whether any particular residues have been established to be important for antigen binding, such as to be a Specificity Determining Residue. Amino acid differences outside the CDRs, or differences due to glycosylation patterns or post translational modifications do not result in different monoclonal antibodies. Changes in antibody structure that do not constitute differences between two monoclonal antibody products with the same CDRs include changes in the FWRs (i.e., humanizing a non-human derived monoclonal antibody or engineering certain framework residues that are important for antigen contact or for stabilizing the binding site, or changes in the constant region (i.e., changing the class or subclass of the constant region, changing specific amino acid residues which might alter an effector function, or changing the species from which the constant region is derived).

Substantially pure: For the purpose of the present invention, substantially pure refers to a homogeneous preparation preferably of a GMF-B antibody or antibody fragment, or other chemical or biological agents. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

2. Antibodies and Antibody Fragments

The present invention includes antibodies and antibody fragments capable of binding preferential for GMF-B antigens. Antibodies or antibody fragments include those that are specific or preferentially selective for at least one GMF-B form. In certain embodiments, the antibodies and fragments thereof can be used to detect a soluble and/or secreted form of a GMF-B protein. A soluble GMF-B protein has a molecular weight of about 17 kDa, as measured by gradient polyacrylamide gel electrophoresis.

In certain embodiments, the antibodies and antibody fragments are capable of binding to a soluble form of GMF-B (sGMF-B) with a specific affinity of between $10^{-8}$ M and $10^{-11}$ M; an antibody or antibody fragment capable of binding to a sGMF-B in a cell; an antibody or antibody fragment capable of selectively reducing the activity of a soluble GMF-B in a cell; and/or an antibody or antibody fragment capable of preferentially binding to a sGMF-B.

An antibody or antibody fragment can be any antibody or antibody fragment and, without limitation, can be a monoclonal antibody, a chimeric antibody, a humanized antibody, or an antibody conjugate.

In an aspect, an antibody or antibody fragment can be any gamma globulin protein found in blood or other bodily fluids of vertebrates, and used by the host immune system to identify and neutralize foreign objects, such as bacteria and viruses. In one aspect, the antibody or antibody fragment can be selected from an antibody, a monoclonal antibody, a chimeric antibody, a humanized antibody, or an antibody conjugate. In an aspect, an antibody or antibody fragment can be any type of immunoglobulin protein, such as IgA, IgD, IgE, IgG or IgM.

In one aspect, an antibody or antibody fragment is capable of reducing the activity of GMF-B in at least one form, including a soluble form. In another aspect, an antibody or antibody fragment is capable of reducing the activity of GMF-B in a secreted form. GMF-B activity is determined by measuring the poly(rC) binding of a sample. In an aspect, the poly(rC)-binding assay is carried out using a gel-shift assay as described in Ausubel FM, (1994). *Current Protocols in Molecular Biology*. Chichester: John Wiley and Sons.

In another aspect of the present invention, an antibody or antibody fragment is capable of preferentially binding to a secreted form of GMF-B protein. In one aspect of the present invention, an antibody or antibody fragment is capable of preferentially binding to a soluble form of GMF-B protein. In another aspect of the present invention, an antibody or antibody fragment is capable of binding to a secreted and soluble form or forms of GMF-B protein. In such aspects, such preferential binding GMF-B can be relative to any other protein. In a particular aspect, such preferential binding to GMF-B is relative to GMF-B that is nuclear bound or associated. In another particular aspect, such preferential binding to GMF-B is relative to GMF-B that is nuclear bound or associated. In another aspect of the present invention, antibodies or antibody fragments can be used to detect a secreted form of GMF-B. In another aspect of the present invention, antibodies or antibody fragments can be used to detect a soluble and secreted form or forms of GMF-B.

In an aspect of the present invention, preferential binding is relative to background. In another aspect, the preferential binding is at least 2-fold, 3-fold, 4-fold, 5-fold, 10-fold, 100-fold, 1.000-fold, 10.000-fold or 1,000,000-fold. In another aspect, an antibody of the present invention preferentially binds a soluble form of GMF-B compared to a nuclear form of GMF-B. In a particular aspect, an antibody of the present invention preferentially binds a soluble form of GMF-B compared to a nuclear form of GMF-B, or the reverse, in another aspect. A binding of the antibody can be measured in any way, and a preferred methodology is a gel-shift assay, set forth in Ausubel.

In an aspect, an antibody or antibody fragment binds GMF-B or a particular form of GMF-B such as a soluble form, a secreted form, and/or a nuclear bound form with a specific affinity of greater than $10^{-7}$M, $10^{-8}$M, $10^{-9}$M, $10^{-10}$M, or $10^{-11}$M, between $10^{-8}$M-$10^{-11}$M, $10^{-9}$M-$10^4$ m and $10^{-10}$M-$10^{-11}$M. In a preferred aspect, specific activity is measured using a competitive binding assay as set forth in Ausubel.

Antibodies and antibody fragments can optionally be immobilized on a solid phase, detectably labeled, or conjugated to a cytotoxic radionuclide, a cytotoxic drug, or a cytotoxic protein and the like.

Antibodies and antibody fragments of the present invention can target expression of GMF-B antigen by cells, preferably human cells, more preferably human cancer cells, such as solid tumors of human breast, ovary, cervix, prostate, colon, stomach, kidney, liver, head, neck, lung, blood, pancreas, skin, testicle, thyroid and brain cancer cells, most preferentially human breast, ovary, head, neck, and brain, in particular human breast cells. Expressed GMF-B antigens can include any form of the gene product, although particularly preferred aspects relate to the detection of the soluble or secreted form of GMF-B. Such antigens can also include gene produced homologues of the GMF-B gene and modified GMF-B antigens expressed by cancer cells.

In one aspect, the antibodies and antibody fragments include those capable of binding to the GMF-B epitopes comprising or consisting of SEQ ID NO: 15, SEQ ID NO: 16 or SEQ ID NO: 17 or fragments of these amino acids. In another aspect, antibodies or antibody fragments can preferentially be used to detect the GMF-B epitopes comprising or consisting of SEQ ID NO: 15, SEQ ID NO: 16 or SEQ ID NO: 17 or fragments of these amino acid sequences. The invention also includes antibodies and antibody fragments specific to GMF-B expression products that contain antigen binding sites that are substantially homologous to these, or that result in substantially similar binding properties. Such antibodies or fragments thereof can be capable of binding to epitopes that are 95%, 90%, 85%, or 80% identical to one or more of the GMF-B epitopes comprising or consisting of SEQ ID NO: 15, SEQ ID NO: 16 or SEQ ID NO: 17 or fragments of these amino acids.

Figure 7D:
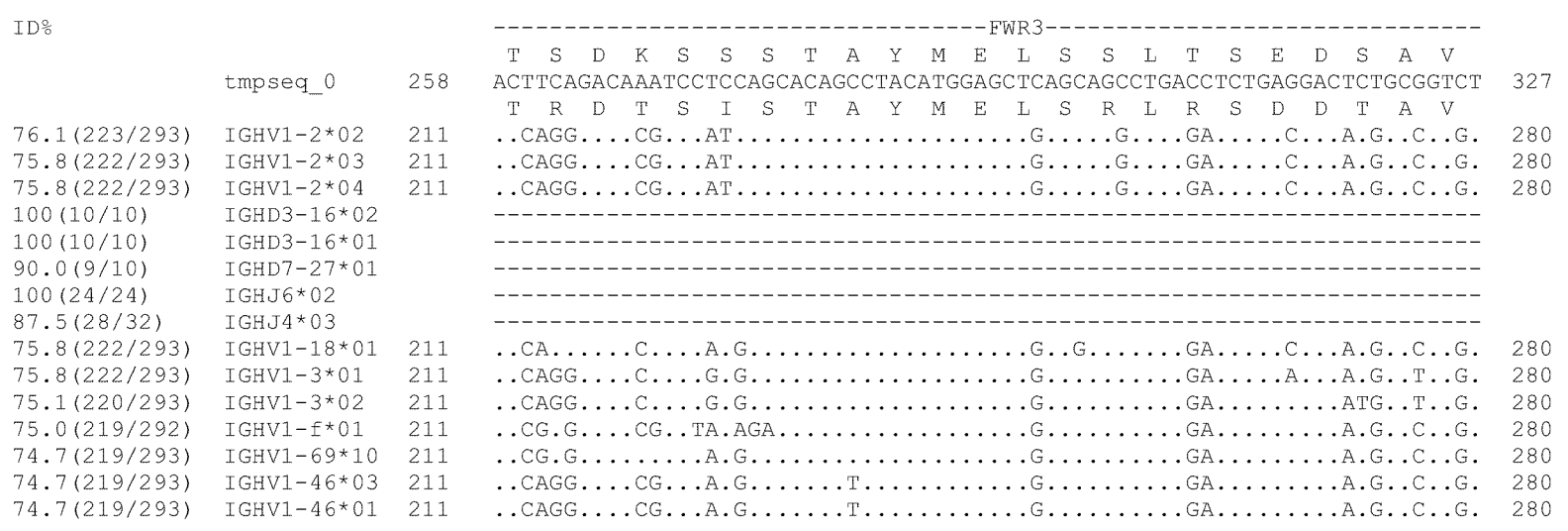
Figure 8C:
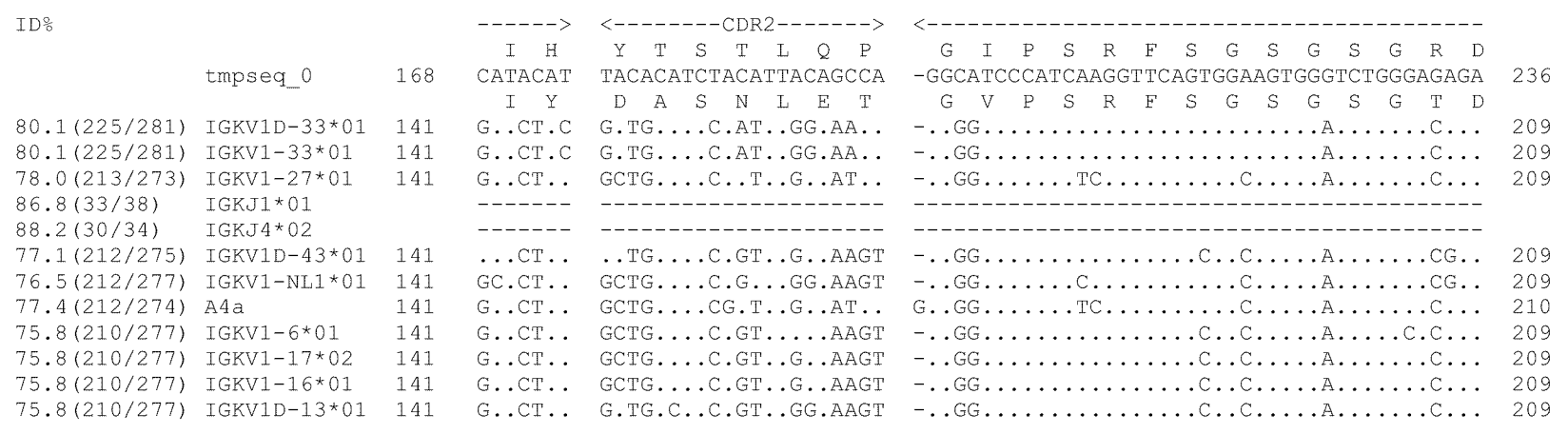

In another aspect, the present invention includes an antibody or an antibody fragment with preferential binding for a GMF-B antigen, including at least one of the heavy chain CDR antigen binding site amino acid sequences CDR1, CDR2, and CDR3 (SEQ ID NOs: 2, 3, and 4) as set forth in FIG. 7, and at least one of the light chain CDR antigen binding site amino acid sequences CDR1, CDR2 and CDR3 (SEQ ID NOs.: 6, 7, and 8) as set forth in FIG. 8. The present invention also includes an antibody with preferential binding for a GMF-B antigen, comprising one or more of the heavy chain CDR antigen binding site amino acid sequences set forth in FIG. 7, and one or more of the light chain CDR antigen binding site amino acid sequences set forth in FIG. 8.

The present invention includes GMF-B antibodies or antibody fragments having antigen binding sites with one or more of CDR1, CDR2, and CDR3, from both heavy and light chains, as described in FIGS. 7 and 8. An antibody or antibody fragment may include any single CDR shown in FIGS. 7 and 8, alone or in combination. By way of example, an antibody or antibody fragment may include CDR1 and CDR2 from both heavy and light chains of FIGS. 7 and 8 (SEQ ID NOs.: 2, 3, 6, and 7, respectively). In other embodiments, an antibody or antibody fragment may include CDR1, CDR2, CDR3 from both heavy and light chains of FIGS. 7 and 8 (SEQ ID NOs.: 2, 3, 4, 6, 7, and 8, respectively). In yet other embodiments, an antibody or antibody fragment may include the full heavy and light chain sequences illustrated in FIGS. 7 and 8 (SEQ ID NOs.: 1, 21 and 5, 39).

The invention also includes antibodies and antibody fragments specific to GMF-B expression products that contain antigen binding sites that are substantially homologous to these, or that result in substantially similar binding properties. Such antibodies or fragments thereof comprises sequences 95%, 90%, 85%, or 80% identical to one or more of the CDR1, CDR2, or CDR3 heavy or light chain from FIGS. 7 and 8. The present invention also includes new hybridoma lines, and the monoclonal antibody molecules that they secrete, which are specific to GMF-B antigen expressed by normal or cancer cells. The present invention also includes chimeric, such as humanized antibodies, and antibody fragments and also includes other modified antibodies and antibody fragments.

In addition to the specific amino acid sequences of the antigen binding sites of the heavy and light chains set forth in FIGS. 7 and 8, the present invention also encompasses antibodies and antibody fragments that have preferential binding to GMF-B antigens but which have FWR and/or CDR antigen binding site amino acid sequences that are not identical to those set forth in FIGS. 7 and 8. Such antibodies and antibody fragments are preferred if they are specific or preferentially selective for the sGMF-B antigen, preferably at least 85% or more as specific, more preferably at least 90% or more as specific, and most preferably at least 95% or more as specific for the sGMF-B antigen as the Alper-sGMF-B mAb or antibody fragment therefor. According to a preferred aspect, a variant of an antibody or antibody fragment of the present invention can be as specific for the GMF-B antigen as a non-variant antibody or antibody fragment of the present invention, or can be more specific.

Antibodies and antibody fragments that are specific to sGMF-B but which have FWR and/or CDR antigen binding site amino acid sequences that are not identical to those set forth in FIGS. 7 and 8 can possess the same or different specificity determining regions (SDRs) as the FWRs and/or CDRs of FIGS. 7 and 8 are included (set forth in bold, underlined text in these figures).

Modifications to the amino acid sequences of the antigen binding sites CDR1, CDR2, and CDR3 set forth in FIG. 7 (heavy chain) and FIG. 8 (light chain) can occur in either or both of the FWR and CDR sequences. According to certain aspects of the invention, variations in antibodies or antibody fragments can occur where they have substantially homologous amino acid sequences, antibodies having substantially similar binding properties, or both.

Humanized variants of the antibodies or antibody fragments of the invention can contain a reduced murine content, and potentially, reduced immunogenicity, when compared to murine antibodies, such as Alper-sGMF-B mAb, or antibody fragments thereof. Humanized variants include those that retain a binding affinity that is substantially similar to that of the original antibody or antibody fragment. An aspect of the invention provides CDR variants of humanized GMF-B antibodies or antibody fragments in which 1, 2, 3, 4, 5, or 6 (three heavy chain and three light chain) CDRs are humanized. A second aspect of the invention provides SDR variants of humanized GMF-B antibodies and antibody fragments in which only Specificity Determining Residues (SDRs) of at least one CDR from the GMF-B antibodies and antibody fragments are present in the humanized antibodies. The SDRs are selected from Table 1 or Table 2.

TABLE 1

Specificity-Determining Residues in Alper-sGMF-B mAb Heavy Chain (SEQ ID NO. 1 and 21).

| Position | Residue |
|---|---|
| 4 | Q |
| 8 | P |
| 10 | L |
| 11 | V |
| 19 | M |
| 30 | S |
| 32 | V |
| 37 | K |
| 39 | K |
| 47 | I |
| 49 | Y |
| 53 | Y |
| 54 | N |
| 55 | E |
| 58 | K |
| 60 | N |
| 61 | E |
| 64 | K |
| 66 | K |
| 67 | A |
| 69 | L |
| 71 | S |
| 73 | K |
| 75 | S |
| 84 | S |
| 86 | T |
| 88 | E |

TABLE 1-continued

Specificity-Determining Residues in Alper-sGMF-B mAb Heavy Chain (SEQ ID NO. 1 and 21).

| Position | Residue |
|---|---|
| 90 | S |
| 98 | S |
| 99 | T |
| 100 | M |
| 101 | I |
| 102 | T |
| 103 | T |
| 104 | G |
| 105 | F |
| 106 | A |
| 107 | Y |
| 108 | W |
| 109 | G |
| 110 | Q |
| 111 | G |
| 112 | T |
| 113 | T |
| 114 | V |
| 115 | T |

Residues 98-115 disclosed as SEQ ID NO: 18.

TABLE 2

Specificity-Determining Residues in Alper-sGMF-B mAb Light Chain (SEQ ID NO. 5 and 39).

| Position | Residue |
|---|---|
| 3 | L |
| 15 | L |
| 17 | G |
| 18 | K |
| 24 | K |
| 30 | N |
| 31 | K |
| 33 | I |
| 34 | A |
| 38 | H |
| 42 | E |
| 43 | G |
| 45 | R |
| 49 | H |
| 50 | Y |
| 51 | T |
| 52 | T |
| 55 | Q |
| 56 | P |
| 58 | I |
| 69 | R |
| 71 | Y |
| 72 | S |
| 74 | S |
| 76 | T |
| 77 | N |
| 79 | E |
| 89 | L |
| 95 | W |
| 96 | T |
| 97 | F |
| 98 | G |
| 99 | G |
| 100 | G |
| 101 | T |
| 102 | K |
| 103 | L |
| 104 | E |
| 105 | I |
| 106 | K |

Residues 95-106 disclosed as SEQ ID NO: 19.

CDR variants can be formed by replacing at least one CDR of a humanized GMF-B antibody and antibody fragments with a corresponding CDR from a human antibody. CDR variants in which one, two, three, four, five, or six CDRs are replaced by a corresponding CDR from a human antibody and retain biological activity that is substantially similar to the binding affinity of the parental GMF-B mAb. CDR variants of the invention can have a binding affinity that is 25% more than the binding affinity of the parental sGMF-B antibody or antibody fragment, more preferably is more than 50%, most preferably at least 75% or 90%.

CDR variants can have altered immunogenicity when compared to GMF-B antibodies and antibody fragments can be formed by grafting all six (three heavy chain and three light chain) CDRs from the GMF-B antibodies and antibody fragments of the present invention onto the variable light ($V_L$) and variable heavy ($V_H$) frameworks of human antibodies and antibody fragments. However, less than all six of the CDRs of the GMF-B antibodies and antibody fragments of the present invention can be present, while still permitting an antibody of the present invention to retain activity. Residues that are directly involved in antigen contact, such as Specificity Determining Residues (SDRs), can be refined. SDR variants are formed by replacing at least one SDR of the GMF-B antibody or antibody fragment with a residue at a corresponding position from a human antibody. It should be noted that not all CDRs must include SDRs.

In a preferred aspect, the variants of the present antibodies and antibody fragments include a combination of CDR and/or SDR substitutions to generate variants having reduced immunogenicity in humans and a binding affinity that is substantially similar to that of the parental antibody or antibody fragment to sGMF-B.

In addition to variants specifically described herein, other "substantially homologous" modified immunoglobulins can be readily designed and manufactured using various recombinant DNA techniques. For example, the framework regions (FWRs) can be varied at the primary structure level. Moreover, a variety of different human framework regions can be used singly or in combination as a basis for the variant. In general, modifications of the genes can be readily accomplished by a variety of techniques, such as site-directed mutagenesis and random mutagenesis.

Alternatively, polypeptide fragments comprising only a portion of the primary antibody structure can be produced where the fragment substantially retains the immunoreactivity properties of the variant. Such polypeptide fragments include fragments produced by proteolytic cleavage of intact antibodies or fragments produced by inserting stop codons at the desired locations nucleotide sequence using site-directed mutagenesis. Single chain antibodies and fusion proteins which include at least an immunoreactivity fragment of the variant are also included within the scope of the invention.

The antibodies and their variants in accordance with the present invention can be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are known in the art. These conjugated antibodies can be incorporated into any composition, including pharmaceutical compositions for use in treating diseases characterized by the expression of GMF-B, including cancer, such as cancer of the breast, ovary, cervix, prostate, colon, stomach, kidney, liver, head, neck, lung, blood, pancreas, skin, testicle, thyroid and brain, most preferentially human breast, ovary, head, neck, and brain, in particular human breast cells. The pharmaceutical compositions are preferably administered to a mammal, more preferably a human patient in need of such treatment, in order to treat the disease.

Antibodies and antibody fragments can either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available.

3. Nucleic Acid Molecules and Host Cells

Any of the antibodies or antibody fragments of the present invention can be encoded by nucleic acids. The present invention includes such molecules, fragments of such molecules and such molecules included in vectors and the like. Nucleic acid molecules also include the complement of such nucleic acid molecules. Both DNA and RNA molecules are examples of nucleic acid molecules.

In another aspect, the present invention provides an isolated DNA sequence which encodes the heavy chain of an antibody molecule, where the antibody molecule has preferential binding for GMF-B antigens, including at least sGMF-B, and where the variable domain of the heavy chain comprises a CDR having the antigen binding site amino acid sequences of at least one, two or all three CDR1, CDR2, and CDR3 set forth in FIG. 7.

In yet another aspect, the present invention provides an isolated DNA sequence which encodes the light chain of an antibody molecule, where the antibody molecule has preferential binding for GMF-B antigens, including at least sGMF-B, and further where the variable domain of the light chain comprises a CDR having the antigen binding site amino acid sequences of at least one, two or all three CDR1, CDR2, and CDR3 set forth in FIG. 8.

In another aspect, the present invention includes a nucleic acid molecule in a host cell. Such nucleic acid molecule can be integrated into the genome of the host cell or can be present on a vector such as a plasmid or viral vector. A nucleic acid molecule of the present invention may be transiently present in such a host cell. In one aspect, a host cell is selected from the group *E. coli; Bacilli*, including *Bacillus subtilis*; enterobacteriacae, including *Salmonella, Serratia* and *Pseudomonas*, yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines. In one aspect, a host cell is selected from a breast cancer cell line such as SKBR3, MCF-7, MDA-MB-231, MDA-MB-435, and ZR75B cells. In another aspect, a host cell is selected from a prostate cancer cell line such as PC3, DU145 and LNCap cells.

4. Methods of Making GMF-B Antibodies or Antibody Fragments

GMF-B antibodies or antibody fragments of the present invention can be developed, for example, using the human breast cancer cell line SKBR3 (available from the American Type Culture Collection as ATCC No. HTB30).

The present invention includes processes for producing monoclonal, chimeric, including humanized antibodies using recombinant DNA technology. See, for example, *Antibodies,*

*A Laboratory Manual* (Harlow & Lane Eds., Cold Spring Harbor Press, 1988), which is herein incorporated by reference in its entirety.

GMF-B antibodies or antibody fragments of the present invention can be produced by any known method including, without limitation, generating murine hybridomas which produce antibodies or antibody fragments specific for GMF-B. Hybridomas can be formed, for example, by the fusion of a mouse fusion partner cell and spleen cells from mice immunized against native sGMF-B prepared without fixation. Mice can be also immunized with crude or semi-purified preparations containing an antigen of interest, such as a native sGMF-β isolated without fixation. To immunize the mice, a variety of different conventional protocols can be followed. For example, mice can receive primary and boosting immunizations of antigenic preparations.

Cell fusions can be accomplished by any procedures known to those skilled in the field of immunology. Fusion partner cell lines and methods for fusing and selecting hybridomas and screening for antibodies or antibody fragments are known.

Antibodies or antibody fragments of the present invention can be produced in large quantities, for example, by injecting hybridoma cells secreting the antibody into the peritoneal cavity of mice and, after appropriate time, harvesting the ascites fluid which contains a high titer of the antibody or antibody fragment, and isolating the antibody or antibody fragment therefrom. Alternatively, the antibodies and antibody fragments can be produced by culturing hybridoma cells in vitro and isolating the secreted antibody or antibody fragment from the cell culture medium.

GMF-B antibodies or antibody fragments of the present invention can also be produced by expressing the appropriate DNA sequence in a host after the sequence has been operably linked to an expression control sequence. Such expression vectors are often replicable in a host organism either as episomes or as an integral part of the host chromosomal DNA. Expression vectors often contain expression control sequences compatible with the host cell, such as an origin of replication. In addition, an expression vector can include a promoter to control expression of the gene, optionally, with operator sequences, and have ribosome binding site sequences and the like for initiating and completing transcription and translation. Suitable promoters include, without limitation, the polyhedrin promoter, lactose promoter system, a tryptophan promoter system, a beta-lactamase promoter system, or a promoter system from phage lambda. Expression vectors can also contain selection markers. DNA sequences encoding the light chain and heavy chain of an sGMF-B antibody or antibody fragments can be inserted into separate expression vectors, or into the same expression vector.

Suitable hosts include, without limitation, prokaryotic strains such as *E. coli*; *Bacilli*, including *Bacillus subtilis*; enterobacteriacae, including *Salmonella, Serratia* and *Pseudomonas*. Suitable hosts also include eukaryotic hosts such as yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines. Other suitable hosts can also be used in accordance with known expression techniques.

The vectors containing the DNA segments of interest can be transferred into the host cell by any method, which varies depending on the type of cellular host. For example, calcium chloride transfection, calcium phosphate treatment, electroporation or cationic liposome mediated transfection (such as DOTAP). Successfully transformed cells, can be identified by a variety of techniques for detecting the binding of a receptor to a ligand.

Expressed gene products can be purified according to any method, including, without limitation, ammonium sulfate precipitation, affinity columns, column chromatography, and gel electrophoresis. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

Isolated or purified DNA sequences can be incorporated into a cloning or expression vector, which can in turn be used to transform a host cell. The transformed host cells can be used in a process for the production of an antibody molecule having specificity for GMF-B antigens, including culturing the host cells and isolating the antibody molecules they produce.

5. Diagnostic Methods, Assays, and Kits

In a further aspect, the present invention includes an immunoassay for preferentially detecting a sGMF-B antigen comprising an antibody or antibody fragment of the present invention.

The present invention also includes an immunoassay for preferentially detecting one or more GMF-B antigens, including a sGMF-B antigen, which bind to a monoclonal antibody having one or more of the heavy chain CDR antigen binding site amino acid sequences set forth in FIG. 7, and one or more of the light chain CDR antigen binding site amino acid sequences set forth in FIG. 8.

Such immunoassays can be used in any suitable manner, including, without limitation, by comprising: (a) contacting the sample with an effective binding amount of one of the antibodies or antibody fragments of the invention; and (b) detecting the antigen by detecting the binding of the antibody to a GMF-B antigen Immunoassays of the present invention can be used to detect cancer cells expressing a GMF-B antigen, particularly cancer, tumor, carcinoma cells or neoplastic disease cells selected from the group consisting of breast, ovarian, cervical, prostate, colon, stomach, kidney, liver, head, neck, lung, blood, pancreatic, skin, testicular, thyroid and brain cancers, most preferentially human breast, ovary, head, neck, and brain, in particular human breast cells.

In a further aspect, the present invention provides a kit for the immunohistochemical detection of carcinoma comprising: (a) an antibody or antibody fragment of the present invention; and (b) a secondary antibody conjugated to a detectable label.

In a further aspect, the present invention provides a kit for the immunohistochemical detection of carcinoma comprising: (a) a monoclonal antibody having one or more of the heavy chain CDR antigen binding site amino acid sequences set forth in FIG. 7, and one or more of the light chain CDR antigen binding site amino acid sequences set forth in FIG. 8; and (b) a secondary antibody conjugated to a detectable label.

Kits can include reagents for assaying a sample for a GMF-B antigen, where such kits may include: sGMF-B antigen specific affinity reagents, such as an antibody, or fragment or mimetic thereof, and/or immunoassay devices comprising the same members of a signal producing system, such as antibodies, enzyme substrates, and the like; various buffers for use in carrying out the subject detection assays; a reference for determining the amount of one or more GMF-B antigens in a sample; and the like. Other examples of kits or kit formats are found in Alper, US Publication No. 2008/0293162, herein incorporated by reference in its entirety.

In further aspect, the present invention provides a method for diagnosing cancer in humans comprising: (a) removing a specimen from a patient suspected of having a cancer; (b) contacting the specimen with an antibody or antibody fragment of the present invention; (c) labeling the specimen; and (d) detecting the presence of the antigen-antibody complex by the label. Such a method of diagnosing cancer can be performed in vivo or in vitro.

In a still further aspect, the present invention provides a method for diagnosing cancer in humans comprising: (a) removing a specimen from a patient suspected of having a cancer; (b) contacting the specimen with a monoclonal antibody having one or more of the heavy chain CDR antigen binding site amino acid sequences set forth in FIG. 7, and one or more of the light chain CDR antigen binding site amino acid sequences set forth in FIG. 8; (c) labeling the specimen; and (d) detecting the presence of the antigen-antibody complex by the label. The method of diagnosing cancer can be performed in vivo or in vitro.

The cancers being diagnosed include those that are selected from the group consisting of solid tumors of the breast, ovary, cervix, prostate, colon, stomach, kidney, liver, head, neck, lung, pancreas, skin, testicle, thyroid and brain, most preferentially human breast, ovary, head, neck, and brain, in particular human breast cells.

In an aspect, sGMF-B levels are higher in early-stage Alzheimer's disease patients relative to age-matched healthy controls. In another aspect, sGMF-B levels are higher in middle-stage Alzheimer's disease patients relative to age-matched healthy controls. In a third aspect, sGMF-B levels are higher in late-stage Alzheimer's disease patients relative to age-matched healthy controls. In one aspect, the level of sGMF BETA are higher in early-stage Alzheimer's disease patients relative to age-matched healthy controls, and similar to healthy control levels during the late stage of Alzheimer's disease. An increase in sGMF-B levels means that they are statistically significant relative to an age-matched healthy controls. Levels similar to healthy control levels can mean that the levels are not statistically significant. In an aspect, the statistically significant differences in levels of sGMF-B have a p-value of $p<0.05$ as measured by the Mann-Whitney test. In another aspect, the statistically significant differences in levels of sGMF-B have a p-value of $p<0.01$ as measured by the Mann-Whitney test. In a further aspect, the statistically significant differences in levels of sGMF-B have a p-value of $p<0.005$ as measured by the Mann-Whitney test.

In a further aspect, the statistically significant differences in levels of sGMF-B have a p-value of $p<0.001$ as measured by the Mann-Whitney test.

In a further aspect, the present invention provides a method for diagnosing Alzheimer's Disease in a subject in need thereof comprising: (a) contacting a specimen from said subject with an antibody or antibody fragment of the present invention; (b) labeling the specimen; and (c) detecting an increase of sGMF-B in a patient with AD, where such AD can be in early-stage, mid-stage, or late-stage. Most preferably, early- or mid-stage AD. Such a method of diagnosing cancer can be performed in vivo or in vitro.

In a still further aspect, the present invention provides a method for diagnosing Alzheimer's Disease in humans comprising: (a) removing a specimen from a patient suspected of having a cancer; (b) contacting the specimen with a monoclonal antibody having one or more of the heavy chain CDR antigen binding site amino acid sequences set forth in FIG. 7, and one or more of the light chain CDR antigen binding site amino acid sequences set forth in FIG. 8; (c) labeling the specimen; and (d) detecting the presence of the antigen-antibody complex by the label. The method of diagnosing cancer can be performed in vivo or in vitro.

The Alzheimer's Disease being diagnosed can be any of early-, mid- or late-stage Alzheimer's Disease a combination thereof.

In an additional aspect, the present invention includes a method for developing drugs useful in treating, diagnosing, or both treating and diagnosing diseases characterized by the expression of gene products of GMF-B and homologues thereof, including identifying gene products expressed by GMF-B and homologues thereof, and utilizing the gene products as biomarkers in the development and identification of drugs selected from the group consisting of sGMF-B antibodies and antibody fragments, inhibiting peptides, siRNA, antisense oligonucleotides, vaccines, and chemical compounds, which specifically target the gene products.

An antibody or antibody fragment of the present invention can also be used in diagnosis of diseases characterized by the expression of sGMF-B, such as cancer. For example, in vivo diagnosis and imaging of a solid tumor of the breast, ovary, cervix, prostate, colon, stomach, kidney, liver, head, neck, lung, blood, pancreas, skin, testicle, thyroid or brain and combinations thereof, most preferentially human breast, ovary, head, neck, or brain and combinations thereof, in particular human breast cells, that expresses sGMF-B can be performed in accordance with the methods of the invention. An antibody or antibody fragment of the present invention can also be used for diagnosis in vitro, for example, by using an antibody or antibody fragment to detect the presence of the cancer marker sGMF-B in a fluid or tissue sample.

Antibodies and antibody fragments can be used in immunoassays to screen body fluids, such as serum, sputum, effusions, urine, cerebrospinal fluid, and the like, for the presence of sGMF-B. Antibodies and antibody fragments can be used for scanning or radioimaging, when labeled with an appropriate radiolabel, to detect primary or metastatic foci of tumor cells. Furthermore, the antibodies are useful in lymphoscintigraphy to detect lymph node involvement in the disease.

A GMF-B antibody or antibody fragment, which can include any or all of the antibodies or antibody fragments specific for GMF-B-related gene products, and/or chimeric, such as humanized, or other variants thereof, can be used therapeutically, or in developing and performing assays, in vivo or in vitro diagnostic procedures, and imaging. The antibodies can be used alone or in combination with a pharmaceutically-acceptable or diagnostic carrier formulation. GMF-B antibodies or antibody fragments can be incorporated into a pharmaceutically or diagnostically acceptable, non-toxic, sterile carrier as a suspension or solution. They can be used as separately administered compositions or given in conjunction with chemotherapeutic or immunosuppressive agents.

The present invention includes therapeutic and diagnostic compositions comprising an antibody or antibody fragment of the present invention in combination with a pharmaceutically acceptable excipient, diluent or carrier. The present invention also includes a process for preparation of a therapeutic or diagnostic composition comprising admixing an antibody molecule of the present invention together with a pharmaceutically acceptable excipient, diluent or carrier. An antibody molecule can be the sole active ingredient in the therapeutic or diagnostic composition, or can be accompanied by other active ingredients including other antibody ingredients, for example anti-T cell, anti-IFNγ or anti-LPS antibodies, or non-antibody ingredients such as xanthines.

Compositions can be incorporated into kits for diagnosing or treating diseases characterized by the expression of GMF-B, including, without limitation, solid tumors, and particularly solid tumors of the breast, ovary, cervix, prostate, colon, stomach, kidney, liver, head, neck, lung, pancreas, skin, testicle, thyroid and brain, most preferentially human breast, ovary, head, neck, or brain, in particular human breast cells.

Antibodies or antibody fragments of the present invention are useful for immunoassays which detect or quantitate GMF-B or cells bearing GMF-B in a sample. Such an immunoassay typically comprises incubating a biological sample from a subject with a need therefor in the presence of a detectably labeled antibody of the present invention capable of identifying the tumor antigen, and detecting the labeled antibody which is bound in a sample.

In an aspect of the present invention the level, localization of one or more forms of GMF-B, including sGMF-B, can determine, confirm or indicate the status of a cell, collection of cells, sample from a subject in need thereof. As used herein, "confirm" means that based on the level, localization or both of one or more forms of GMF-B, including sGMF-B, in a cell, collection of cells or sample, subject etc provides a sufficient basis to characterize the status of a cell, collection of cells, sample or subject etc. As used herein, "confirm" means that based on the level, localization or both of one or more forms of GMF-B, including sGMF-B, in a cell, collection of cells or sample, subject etc provides in combination with other analysis a basis to characterize the status of a cell, collection of cells, sample or subject etc. As used herein, "indicate" means that based on the level, localization or both of one or more forms of GMF-B, including sGMF-B, in a cell, collection of cells or sample, subject etc provides that more likely than not or greater probability of determining the status of a cell, collection of cells, sample or subject etc. is of a particular status In one aspect, a status of a cell or collection of cells can be determined using an antibody of the present invention or of fragment thereof whether that cell, collection of cells, sample etc. are metastatic tumor cells, non-metastatic tumor cells, from a solid tumor or normal cells. A status of a subject can include whether the analysis provides information on whether a metastatic cancer or non-metastatic tumor is present in the subject.

Examples of confirmatory analysis, assays, tests, such as histological examination of samples, and so forth that can be used to confirm or in combination with those disclosed herein include, without limitation, those set forth in Alper, US Publication No. 2008/0293162.

In an aspect of the present invention the level, localization or both of one or more forms of GMF-B, including sGMF-B, is diagnostic or prognostic of a disease or outcome probability.

In an aspect of the present invention a reduced level of sGMF-B in a cell, collection of cells or sample can diagnose, prognose, determine, confirm or indicate that such derived is from a metastatic tissue. In one aspect, "reduced" can mean reduced relative to a control, with the control being a normal cell of the same type that is non-metastatic. In this aspect, the reduction can be greater than 10, 20, 30, 40, 50, 60, 70, 80, 90, 95, or 99%.

In an aspect of the present invention, a similar level of sGMF-B in a cell, collection of cells or sample to a normal control can diagnose, prognose, determine, confirm or indicate that such cell was derived from a non-metastatic tissue.

In an aspect of the present invention, a lack of localization of sGMF-B in a cell nucleus can diagnose, prognose, determine, confirm or indicate that such derived is from a metastatic tissue.

In an aspect of the present invention, localization of sGMF-B in a cell, collection of cells or sample to a normal control can diagnose, prognose, determine, confirm or indicate that such derived from a non-metastatic tissue.

In an aspect of the present invention, the cell, collection of cells or sample is a cervical or breast cell collection of cells or sample, in particular human breast cells.

Antibodies and antibody fragments of the present invention are also useful for immunopathological analysis, such as the differential diagnosis of tumor type, and the subclassification of the tumor based on its expression or localization of at least one form of GMF-B, including sGMF-B, including, without limitation, assessment of metastatic potential, predicted responses to therapy, and overall prognosis.

GMF-B antibodies and antibody fragments permit the definition of subpopulations of tumor cells among the heterogeneous cells present in a growing tumor and can be used, for example, in the typing and cross-matching of the tumor cell "lines," including, without limitation, by means of flow cytometry, both at the time of surgery and prior to therapy. An analysis of the tumor cell populations or subpopulations with antibodies or antibody fragments of this invention, and a battery of additional antibodies or antibody fragments, can be used to define (a) which antigen preparation would be the most appropriate for specific active immunotherapy, (b) which antibody or antibody fragment or chimeric antibody would be efficacious for the particular cancer; and (c) which antibody or combination of antibodies or antibody fragments should be used for imaging the patient at a later date in search for recurrent or metastatic tumors.

A biological sample can be treated with nitrocellulose, or other solid support or carrier which is capable of immobilizing cells, cell particles or soluble proteins or glycoproteins. The support can then be washed with suitable buffers followed by treatment with the detectably labeled antibody of the present invention. The solid phase support can then be washed with the buffer a second time to remove unbound antibody. The amount of bound label on the solid support can then be detected by conventional means.

One of the ways in which the antibody of the present invention can be detectably labeled is by linking the same to an enzyme and use in an enzyme immunoassay (EIA) or enzyme-linked immunosorbent assay (ELISA). This enzyme, when subsequently exposed to its substrate, will react with the substrate generating a chemical moiety which can be detected, for example, by spectrophotometric, fluorometric or by visual means. In an alternate embodiment, the enzyme is used to label a binding partner for the antibody of the invention. Such a binding partner can be an antibody against the constant or variable region of the antibody of the invention, such as a heterologous anti-mouse immunoglobulin antibody. Alternatively, the binding partner can be a non-antibody protein capable of binding to the antibody of the present invention.

By radioactively labeling the antibodies of the present invention, it is possible to detect GMF-B through the use of a radioimmunoassay (RIA). The radioactive isotope can be detected by such means as the use of a gamma counter or a scintillation counter or by autoradiography. Isotopes which are particularly useful for the purpose of the present invention are known in the art.

It is also possible to label the antibodies of the present invention with a fluorescent compound. When the fluorescently labeled antibody is exposed to light of the proper wavelength, its presence can then be detected due to fluorescence. The antibodies of the present invention also can be detectably labeled by coupling to a chemiluminescent compound. The presence of the chemiluminescently labeled antibody is then determined by detecting the presence of luminescence that arises during the course of a chemical reaction. A bioluminescent compound can also be used to label the antibodies of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and sequorin.

Detection of the antibody, fragment or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards.

In situ detection can be accomplished by removing a specimen from a patient, and providing the labeled antibody, or the unlabelled antibody plus a labeled binding partner to such a specimen. Through the use of such a procedure, it is possible to determine not only the presence of the antigen but also its distribution in the examined tissue. Using the present invention, those of ordinary skill will readily perceive that any of a wide variety of histological methods (such as staining procedures) can be modified in order to achieve such in situ detection. Such methods include, for example, immunohistochemical staining procedures. In an aspect, an avidin-biotin immunoperoxidase staining system can be used, and a kit utilizing this system is also contemplated, although the methods of the present invention can utilize any suitable staining procedures known in the art.

Kits according to the present invention can include frozen or lyophilized antibodies to be reconstituted by thawing or by suspension in a liquid vehicle. The kits can also include a carrier or buffer. Preferably, the kit also comprises instructions for reconstituting and using the antibody. The kit employing antibodies, including chimeric and humanized antibodies of the present invention, can be used for immunohistochemical evaluation of cancers, including cancer of the breast, ovary, cervix, prostate, colon, stomach, kidney, liver, head, neck, lung, blood, pancreas, skin, testicle, thyroid and brain, most preferentially human breast, ovary, head, neck, and brain, in particular human breast cells.

The kits including the reagents necessary for immunohistochemical analysis can be provided as follows: a) GMF-B antibody or antibody fragment of the present invention, or chimeric or humanized variants thereof; b) blocking reagent (in the form of, for example, goat serum) and secondary antibody (such as, for example, goat anti-mouse antibody); c) detectable marker (such as, for example, immunoperoxidase or alkaline phosphatase); and d) developing reagents. The primary antibody (sGMF-B antibody or antibody fragment or variants thereof) serves as an antigen which can bind more than one secondary antibody. The secondary antibodies form a "bridge" between the primary antibody and the complex formed by the detectable marker and developing reagent (for example, a horseradish peroxidase-antiperoxidase complex).

Any suitable detection system can be used in accordance with the methods and kits of the present invention. Such detection systems are widely used in immunofluorescence applications, and can be imaged using techniques including, but not limited to, flow cytometry, microscopy, Western blotting, and ELISAs. Suitable detection systems can employ conjugates of secondary antibodies, conjugates of colloidal gold, or conjugates of secondary proteins, in order to amplify the signal from a primary protein (in the context of the present invention, the primary protein signal being amplified is bound a sGMF-B antibody, which can or cannot be labeled, for example with a protein such as biotin), which is in turn being used to detect a specific target (in the context of the present invention, the target is a GMF-B expression product).

Suitable secondary conjugates for use in the methods and kits of the present invention can include, but are not limited to, enzyme conjugates of a secondary antibody and an enzyme such as horseradish peroxidase or alkaline phosphatase; enzyme conjugates of avidin or streptavidin and an enzyme such as horseradish peroxidase or alkaline phosphatase; enzyme conjugates of protein A or protein G and an enzyme such as horseradish peroxidase or alkaline phosphatase; conjugates of colloidal gold and a secondary antibody; conjugates of colloidal gold and avidin or streptavidin; conjugates of magnetic particles and a secondary antibody; and conjugates of secondary antibodies and labels such as fluorescent dyes and biotin. The present invention is not limited to any particular detection systems, and it is considered within the ability of the person of ordinary skill in the art to utilize these or other detection systems in accordance with the present invention. These secondary conjugates (also referred to as labels in the context of the present invention) are useful for visualizing antigen-antibody complexes.

The antibody or antibody fragment of the present invention can also be adapted for utilization in an immunometric assay, also known as a "two-site" or "sandwich" assay. In a typical immunometric assay, a quantity of unlabelled antibody (or fragment of antibody), is bound to a solid support that is insoluble in the fluid being tested and a quantity of detectably labeled soluble antibody is added to permit detection and/or quantitation of the ternary complex formed between solid-phase antibody, antigen, and labeled antibody.

For purposes of in vivo imaging of breast, ovary, cervix, prostate, colon, stomach, kidney, liver, head, neck, lung, blood, pancreas, skin, testicle, thyroid and brain, most preferentially human breast, ovary, head, neck, and brain, in particular human breast cancer and other cancers using the antibodies or antibody fragments of the present invention, there are many different labels and methods of labeling known to those of ordinary skill in the art. Examples of the types of labels which can be used in the present invention include radioactive isotopes, paramagnetic isotopes, and compounds which can be imaged by positron emission tomography (PET).

6. Pharmaceutical Compositions and Methods of Treatment

Another aspect of the invention provides a composition comprising any of these antibodies, optionally in combination with a pharmaceutically acceptable carrier. In another aspect, an antibody of the present invention is optionally in combination with one or more active agents, drugs or hormones.

The present invention also provides a method of treating human or animal subjects suffering from or at risk of a cancer that expresses GMF-B, such as solid tumors of the breast, ovary, cervix, prostate, colon, stomach, kidney, liver, head, neck, lung, blood, pancreas, skin, testicle, thyroid and brain, most preferentially human breast, ovary, head, neck, and brain, in particular human breast cells, the method comprising administering to the subject a therapeutically effective amount of an antibody of the present invention, or a pharmaceutical composition comprising a therapeutically effective amount of an antibody of the present invention.

The term "subject" as used herein refers to any subject in need of treatment, preferably a human patient or subject.

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs, or primates. The animal model can also be used to determine the appropriate concentration range and route of administration. Such information can then be used to determine useful doses and routes for administration in humans.

An effective amount for a human subject can depend upon the severity of the disease state, the general health of the subject, the age, weight and gender of the subject, diet, time and frequency of administration, drug combination(s), reaction sensitivities and tolerance/response to therapy and can be determined by routine experimentation and is within the judgment of the clinician. Generally, an effective dose will be from 0.01 mg/kg to 50 mg/kg, preferably 0.1 mg/kg to 20 mg/kg, more preferably from about 1 mg/kg to about 15 mg/kg.

Compositions can be administered individually to a patient or can be administered in combination with other agents, drugs or hormones. According to some aspects, antibodies can be conjugated with these agents. A summary of the ways in which the antibodies of the present invention can be used therapeutically includes direct cytotoxicity by the antibody, either mediated by complement or by effector cells, or conjugated to anti-tumor drugs, toxins, and radionuclides. Antibodies can also be used for ex vivo removal of tumor cells from the circulation or from bone marrow.

Cytotoxic proteins can include, but are not limited to, Ricin-A, *Pseudomonas* toxin, Diphtheria toxin, and tumor necrosis factor. Diagnostic radionuclides and cytotoxic agents such as cytotoxic radionuclides, drug and proteins can also be conjugated to the antibodies of the present invention. Examples of radionuclides which can be coupled to antibodies and selectively delivered in vivo to sites of antigen include $^{212}$Bi, $^{131}$I, $^{186}$Re, and $^{90}$Y, among others. Radionuclides can exert their cytotoxic effect by locally irradiating the cells, leading to various intracellular lesions, as is known in the art of radiotherapy. Examples of cytotoxic drugs which can be conjugated to antibodies and subsequently used for in vivo therapy include, but are not limited to, daunorubicin, doxorubicin, methotrexate, and Mitomycin C. Cytotoxic drugs can interface with critical cellular processes including DNA, RNA, and protein synthesis.

A dose at which the antibody molecule of the present invention is administered depends on the nature of the condition to be treated, and on whether the antibody molecule is being used prophylactically or to treat an existing condition. If administered prophylactically, i.e., as a vaccine, the antibody is administered in an amount effective to elicit an immune response in the subject.

If the antibody molecule has a short half-life (e.g. 2 to 10 hours) it can be necessary to give one or more doses per day. Alternatively, if the antibody molecule has a long half life (e.g. 2 to 15 days) it can only be necessary to give a dosage once per day, per week or even once every 1 or 2 months.

A pharmaceutical composition can also contain a pharmaceutically acceptable carrier for administration of the antibody. The carrier should not itself induce the production of antibodies harmful to the individual receiving the composition and should not be toxic. Suitable carriers include those known in the art, and can be selected from large, slowly metabolized macromolecules such as proteins, polypeptides, liposomes, polysaccharides, polylactic acids, polyglycolic acids, polymeric amino acids, amino acid copolymers and inactive virus particles, although suitable carriers are not limited to these examples.

Preferred forms for administration include forms suitable for parenteral administration, e.g. by injection or infusion, for example by bolus injection or continuous infusion. Where the product is for injection or infusion, it can take the form of a suspension, solution or emulsion in an oily or aqueous vehicle and it can contain formulatory agents, such as suspending, preservative, stabilizing and/or dispersing agents. Alternatively, the antibody molecule can be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

A pharmaceutical compositions of this invention can be administered by any number of routes including, but not limited to, oral, intravenous, intramuscular, intra-arterial, intramedullary, intrathecal, intraventricular, transdermal, transcutaneous, subcutaneous, intraperitoneal, intranasal, enteral, topical, sublingual, intravaginal or rectal routes. Hyposprays can also be used to administer the pharmaceutical compositions of the invention. Therapeutic compositions can be prepared as injectables, either as liquid solutions or suspensions. Solid forms suitable for solution in, or suspension in, liquid vehicles prior to injection can also be prepared.

Direct delivery of the compositions will generally be accomplished by injection, subcutaneously, intraperitoneally, intravenously or intramuscularly, or delivered to the interstitial space of a tissue. Dosage treatment can be a single dose schedule or a multiple dose schedule.

When an antibody or antibody fragment composition is to be administered by a route using the gastrointestinal tract, the composition can to contain additional agents which protect the antibody from degradation but which release the antibody once it has been absorbed from the gastrointestinal tract. Such additional agents are well-known to those skilled in the art.

Antibodies of the present invention can also be administered in methods of conducting gene therapy. In order to achieve this, DNA sequences encoding the heavy and light chains of the antibody molecule under the control of appropriate DNA components are introduced into a patient such that the antibody chains are expressed from the DNA sequences and assembled in situ.

7. GMF-B Expression Products as Drug Development Targets

In addition, the present invention relates to the discovery that GMF-B and homologues thereof can cause the expression or change in subcellular localization of sGMF-B antigens by cells in patients suffering from various diseases, such as cancers, and more specifically solid tumors of the breast, ovary, cervix, prostate, colon, stomach, kidney, liver, head, neck, lung, blood, pancreas, skin, testicle, thyroid and brain, most preferentially human breast, ovary, head, neck, and brain, in particular human breast cells. This expression of sGMF-B antigens presents a novel drug development target, and accordingly the present invention also relates to the use of such sGMF-B antigens as biomarkers that can be targeted not only by the sGMF-B antibodies or antibody fragments of the present invention, but also by various other molecules, such as siRNA, antisense oligonucleotides, vaccines, and chemical compounds.

Methods for developing drugs useful in treating and/or diagnosing diseases characterized by the expression of gene products of GMF-B and homologues thereof can include the steps of identifying the gene products expressed by GMF-B and homologues thereof in a subject having a disease, and utilizing those gene products as to development and identify drugs that specifically target the gene products.

Once candidate drugs have been developed based on the GMF-B antigens, the sGMF-B antigens and GMF-B antibodies and antibody fragments of the present invention can be used to aid in screening the various drug candidates, in order to identify those drug candidates that exhibit a desired level of specificity for diseased cells presenting sGMF-B expression products.

The following examples are non-limiting illustrative examples.

Example 1

Alper-GMF-B mAb Molecular Weight

Approximately 1 ug of a purified mAb (identified as anti-sGMF-B) is suspended in PBS, and is applied under reducing (boiled 3 minutes in sample buffer with beta-mercaptoethanol and 10% SDS) to 10% Bis-Tris gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of such gels are taken. Under denatured conditions, the heavy chain of IgG1 Ab (clone name: Alper-GMF-B mAb) is detected at ~50 kDa and light chain of IgG1 (clone name: Alper-GMF-B) is detected at ~25 kDa. See FIG. 1. Molecular weight markers are shown on the left.

Example 2

A 17 kDa MWt Protein is Detected from MDA-MB-231 Culture Supernatant

A 17 kDa MWt protein is detected from MDA-MB-231 culture supernatant when blotted with anti-sGMF-B mAb. See FIG. 2. Samples may be prepared and analyzed as follows.

Sample Preparation and Gel Loading: The protein concentrations of the MDA-MB.231 cell culture supernatant are determined using BCA Assay (Smith et. al. Anal. Biochem. 150: 76-85, 1985, and Pierce Chemical Co., Rockford, Ill.). The samples are then lyophilized, redissolved to 4 mg/ml in SDS Boiling Buffer, and heated in a boiling water bath for 3 minutes before loading onto an 8% acrylamide slab gel.

Western Blotting Methods: Eight % acrylamide slab gel electrophoresis is carried out about 4 hrs at 15 mA/gel. After slab gel electrophoresis, the gel for blotting is placed in transfer buffer (12.5 mM Tris, pH 8.8, 96 mM Glycine, 20% MeOH) and transblotted onto a PVDF membrane overnight at 200 mA and approximately 100 volts/2 gels. The following proteins (Sigma Chemical Co., St. Louis, Mo.) are used as molecular weight standards: myosin (220,000), phosphorylase A (94,000), catalase (60,000), actin (43,000), carbonic anhydrase (29,000) and lysozyme (14,000). The blots are blocked for two hours in 5% nonfat dry milk (NFDM) in Tween-20 tris buffer saline (TTBS) and rinsed in TTBS. Blot is incubated in primary antibody (anti-GMF-beta antibody diluted 1:125 in 2% NFDM TTBS) overnight. The blot is rinsed 3×10 minutes in TTBS, placed in secondary antibody (Sheep anti-mouse IgG-HRP, [Cat# $Na_{931}$V Lot #352104, GE Healthcare] 1:1,000 diluted in 2% NFDM in TTBS) for two hours, rinsed 3×10 minutes in TTBS, treated with ECL, and exposed to x-ray film.

Figure 2:
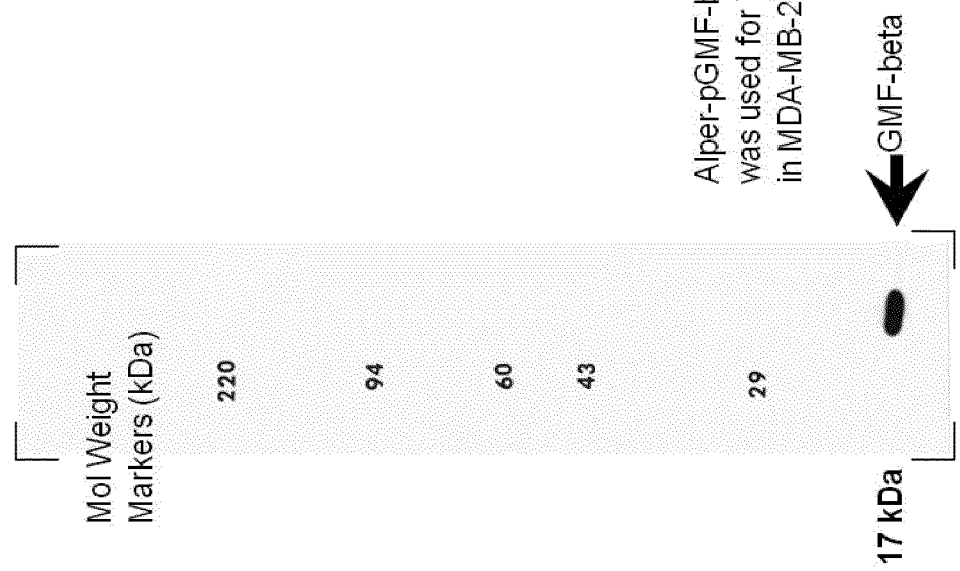
FIG. 2. Western Blot Analysis of MDA-MB-231 cell culture supernatant with Alper-sGMF-B mAb FIG. 3A-3D Immunohistochemical Staining of Breast and Ovarian Cancer Tissue FIG. 4. Breast Cancer Patient GMF-B Levels FIG. 5. Breast Cancer Patient Survival, association of GMF-B Nucleus Overexpression With Overall Survival In Breast Cancer FIG. 6A. Alzheimer's Disease Patient and Control Information FIG. 6B. Alzheimer's Disease Patient Plasma and Control Plasma GMF-B Levels FIG. 7A-7E. Alper-sGMF-B mAb heavy chain sequence information. FWRs and CDRs of the heavy chain of a Alper-sGMF-B mAb, in which the polypeptide sequence provided in the top line (SEQ ID NO: 21) corresponds to the sequence of the Alper-sGMF-B mAb Amino acid residues are numbered using the convention of Kabat et al., (1991) Sequences of Proteins of Immunological Interest, $5^{th}$ Edition, Department of Health and Human Services, Public Health Service, National Institutes of Health, Bethesda (NIH Publication No. 91-3242). Bold residues set forth in underlined text indicate specificity determining residues (SDRs).

As shown in FIG. 2, a protein with a 17 kDa MWt is detected when blotted with anti-pGMF-beta MoAb in culture supernatant prepared from MDA-MB-231 cells.

Example 3 sGMF-B is the Antigen for the Alper-GMF-B mAb

The antigen for Alper-GMF-B mAb is isolated, digested with trypsin, and analyzed by MALDI-MS. The major protein is identified in protein database search as SwissProt gi:4758442: glia maturation factor, beta [*Homo sapiens*]. Table 3 shows results of database search. Protein scores are derived from ions scores as a non-probabilistic basis for ranking protein hits. Based on the probability based mouse scoreing, ions score is −10*Log(P), where P is the probability that the observed match is a random event. Individual ions scores >45 indicate identity or extensive homology (p<0.05). Also present, as likely contaminants, are albumin (fragment) and hemoglobin alpha and beta.

TABLE 3

Example 3 ('Peptide' sequences disclosed as SEQ ID NOS 15-17, respectively, in order of appearance)

gi|4758442 Mass: 16702 Score: 138 Queries matched: 3
glia maturation factor, beta [*Homo sapiens*]

| Query | Observed | Mr(expt) | Mr(calc) | Delta | Miss | Score | Expect | Rank | Peptide |
|---|---|---|---|---|---|---|---|---|---|
| 39 | 501.8065 | 1001.5984 | 1001.5757 | 0.0227 | 0 | 41 | 0.14 | 1 | K.LVQTAELTK.V |
| 49 | 552.7930 | 1103.5714 | 1103.5645 | 0.0070 | 0 | 60 | 0.0018 | 1 | K.ETNNAAIIMK.I |
| 73 | 703.3333 | 1404.6520 | 1404.6521 | −0.0001 | 0 | 36 | 0.41 | 1 | R.NTEDLTEEWLR.E |

Proteins matching the same set of peptides:
gi|13529185 Mass: 18098 Score: 138 Queries matched: 3
GMFB protein [*Homo sapiens*]

Example 4

Purification of GMF-B and Sandwich ELISA

Approximately 2 mg of GMF-B is purified from a cultured human GMF-B cell line or plasma. A preparation of GMF-B is validated by comparison with GMF-B antigen in human plasma and/or cell lines. The purified GMF-B antigen is then used as a standard in a sandwich ELISA assay together with a monoclonal anti-sGMF-B antibody and polyclonal antibodies. In the sandwich format, a capture antibody is coated onto the walls of a microtiter plate, the sample containing the antigen is added, then washed. Captured sample is retained in the well and is then detected by a second, antigen-specific antibody. Anti-sGMF-B mAb (clone name: Alper-GMF-B or Alper-p17) is used as the capture antibody as it is specific to the form of plasma GMF-B found in AD. As a second capturing antibody, commercially available anti-human GMF-B antibodies are used as a secondary antibody, conjugated to horse radish peroxidase, to quantitate GMF-B captured by the capture antibody. A standard colorimetric detection method reagent such as tetramethylbenzidine (TMB) is used.

Example 5

GMF-B is Visualized in AD Brain Tissues, Breast and Ovarian Cancer Tissue Via Immunohistochemical Staining Middle temporal gyrus brain tissue specimens from three histopatholoically-diagnosed AD patients are collected from Yale Autopsy Tissue Service. Microtome sections are deparaffinized and incubated with Anti-sGMF-B mAb (clone name: Alper-GMF-B or Alper-p17) at 1:400 concentration following general immunohistochemistry (IHC) procedures. Diagnostic staining is performed via standard pathological procedures using haematoxylin and eosin (H&E), silver, beta-amyloid and tau antibodies. Results show that GMF-B is predominantly a cytoplasmic protein that is expressed at high levels in observed brain regions. In addition, results show that GMF-B is distributed to a large extent in neurons and to a smaller extent in astrocytes and oligodendrocytes. Within the neurons, GMF-B is found in the cell soma and axonal compartments. GMF-B distribution in vascular structures is observed to vary between patients at different stages of disease.

GMP-B expression is analyzed by immunohistochemistry in 96 breast cancer patients and 12 cases of normal conditions Immunohistochemical staining is performed as follows. Incomplete removal of paraffin can cause poor staining of the section. Accordingly, prior to staining, tissue sections are deparaffinized and rehydrated as follows: immerse slides in xylene and incubate for 2×15 minutes; immerse slides in xylene:ethanol (1:1) for 5 minutes; immerse slides in 100% ethanol for 5 minutes, and follow with 95%, 75% and 50% ethanol for 3 minutes each; rinse slides with reagent-quality water for 5 minutes and keep in water until ready to perform antigen retrieval.

Following deparaffinization and rehydration, antigen is retrieved using heat induced antigen retrieval (HIAR) as follows: fill plastic Coplin Jar/container with Retrieval Buffer; place the Coplin jar/container in steamer; turn on steamer and preheat to 90-100° C.; carefully put slides into the Coplin jar/container and steam for 40 min (95-100° C.); turn off the steamer, remove the Coplin jar/container to room temperature and allow the slides to cool for 20 min; rinse slides with Wash Buffer for 3×3 minutes and begin staining procedure.

The retrieved antigen is then stained for immunohistochemical analysis as follows: tap off excess buffer. Apply enough Peroxidase Blocking Buffer to cover specimen, and incubate for 5 minutes; rinse sections with Washing Buffer for 3×3 minutes; tap off excess buffer. Apply enough Background Block to cover specimen and incubate for 5 minutes; rinse sections with Washing Buffer for 3×3 minutes; tap off excess buffer. Apply enough GMFB antibody (1:50 dilution in antibody diluents) to cover specimen, and incubate for 1 hour; rinse sections with Washing Buffer for 5×3 minutes; tap off excess buffer. Apply enough Mach3 probe to cover specimen, and incubate for 15 minutes; rinse sections with Washing Buffer for 3×3 minutes; tap off excess buffer. Apply enough Mach3 polymers to cover specimen, and incubate for 15 minutes; rinse sections with Washing Buffer for 3×3 minutes; tap off excess washing buffer; apply enough DAB substrate solution to cover specimen, and incubate until desired stain intensity develops; rinse sections in tap water for 3 minutes; immerse slides in hematoxylin solution, incubate 30 sec to 5 minutes; rinse to clear with tap water and follow by dehydration; immerse slides in 70%, 80%, 95%, 100% ethanol for 2 minutes each, and follow in xylene for 2×2 minutes; dry and mount slides.

Figure 3B:
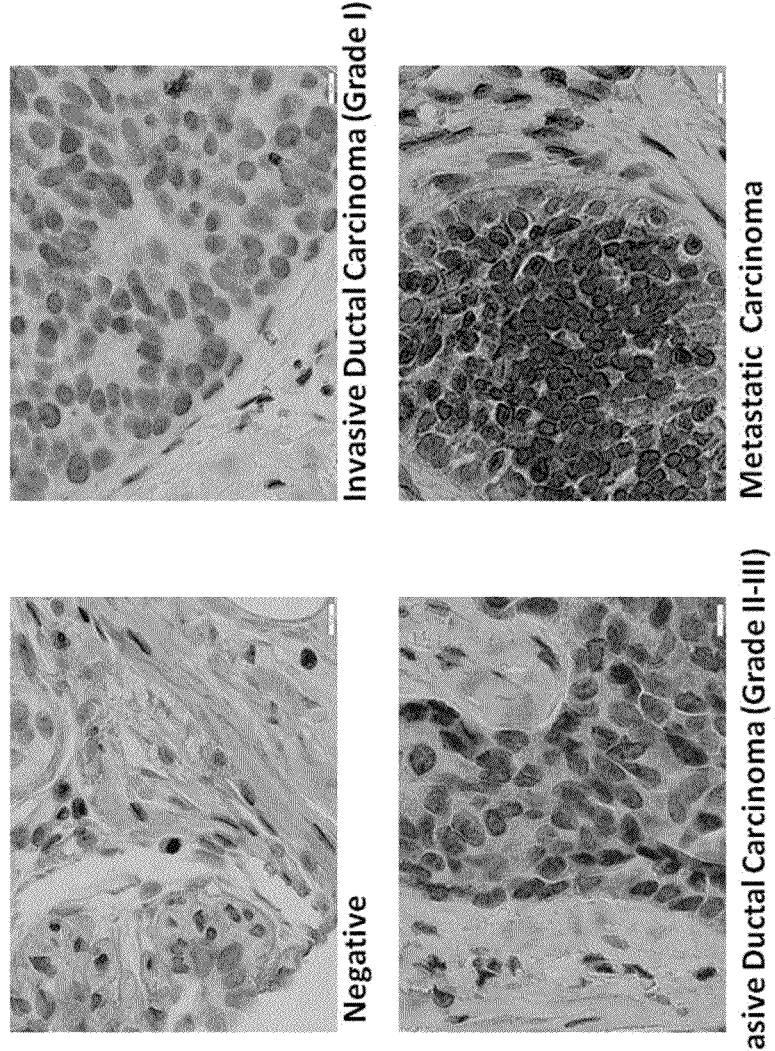
Figure 3C:
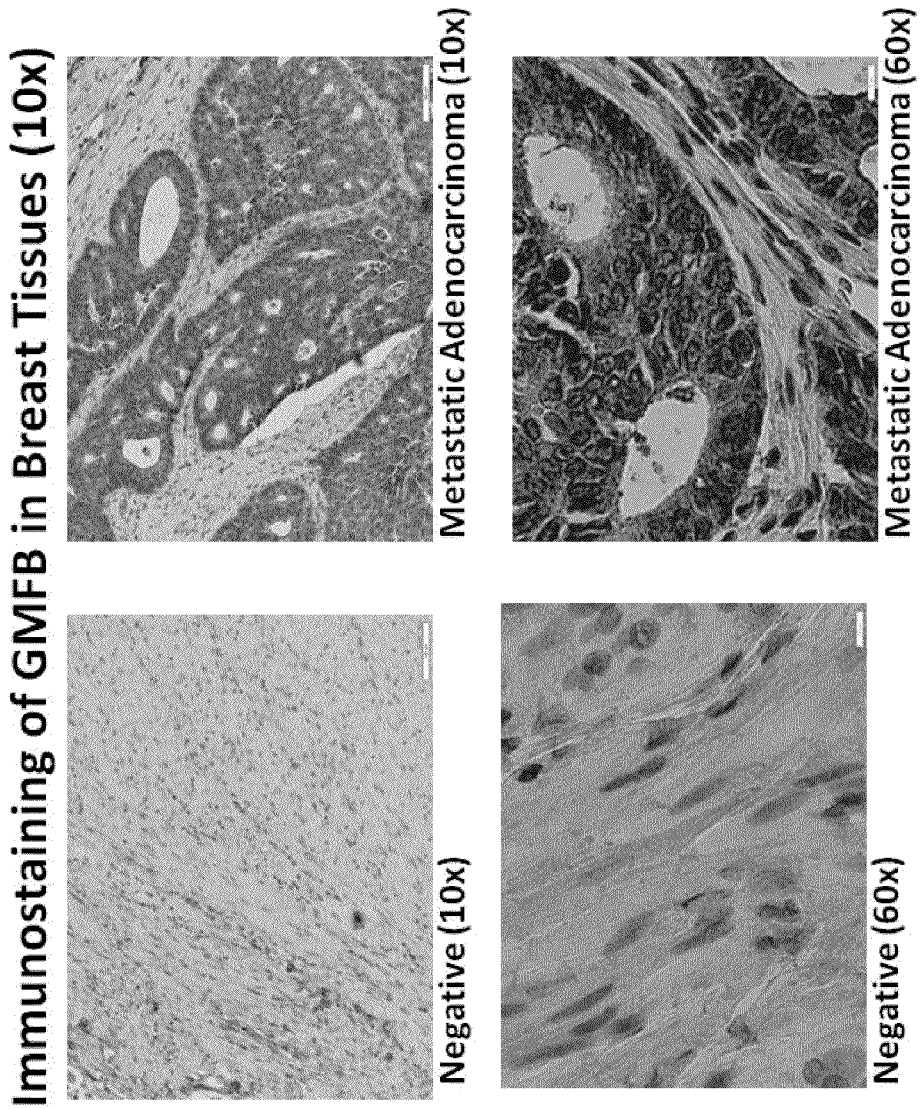
Figure 3D:
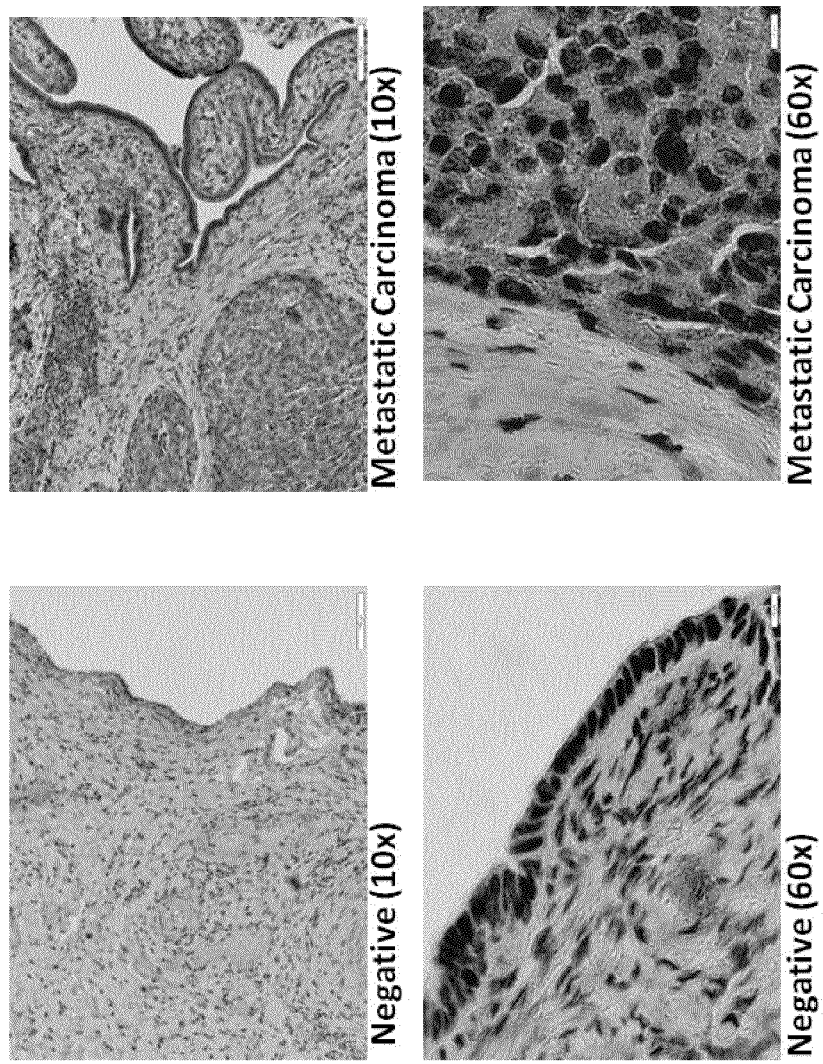

The positive staining both cytoplasmic and strongly nuclear in GMF-B expression was found to be significantly enhanced in invasive ductal breast cancer cells than that in normal cells, normal conditions and was positively correlated with stage, TNM classification. See FIGS. 3A-C. A similar finding was also published for GMF-B, shown in serous ovarian cancer as an independent prognostic predictor (Li Y L, Ye F, Cheng X D, Hu Y, Zhou C Y, Lu W G, Xing X. Identification of glia maturation factor beta as an independent prognostic predictor for serous ovarian cancer. *European J Cancer* 46: 21-4-2118, 2010). See FIG. 3D.

Example 6

Breast Cancer Patients have Higher sGMF-B Levels than Control Groups

Plasma samples are obtained from control and breast cancer patient groups and are diluted with PBS at a ratio of 1:100. Plasma sGMF-B levels are measured with an enzyme-linked immunosorbent enzyme assay. The polysorp ELISA plates (Nalgene NUNC® International, Rochester, N.Y.) are coated with 100 μl/well of diluted plasma and incubated at 4° C. overnight. The blood plasma samples are analyzed in a blinded fashion. Wells are washed with PBS and incubated at room temperature for one hour with blocking buffer (5% BSA in PBS). After washing with PBS, the primary antibody, anti-sGMF-B mAb (clone name: Alper-GMF-B) is added in dilution buffer (45 μg/ml) (PBS buffer, 1% BSA, 0.01% Tween-20). The wells are washed with PBS/0.03% Tween-20 and incubated at room temperature for one hour with 100 μl/well secondary antibody (HRP-Donkey anti-mouse IgG, Jackson ImmunoResearch, West Grove, Pa.) diluted 1:3000. After washing the wells, 100 μl Immunopure TMB substrate solution (Pierce, Rockford, Ill.) is added. Color reaction is stopped by the addition of 100 μl/well 1N $H_2SO_4$ and the analysis is performed with an ELISA Reader. The figure represents optical density (OD) values of plasma readings for sGMF-B levels. See FIG. 4.

Example 7

Figure 5:
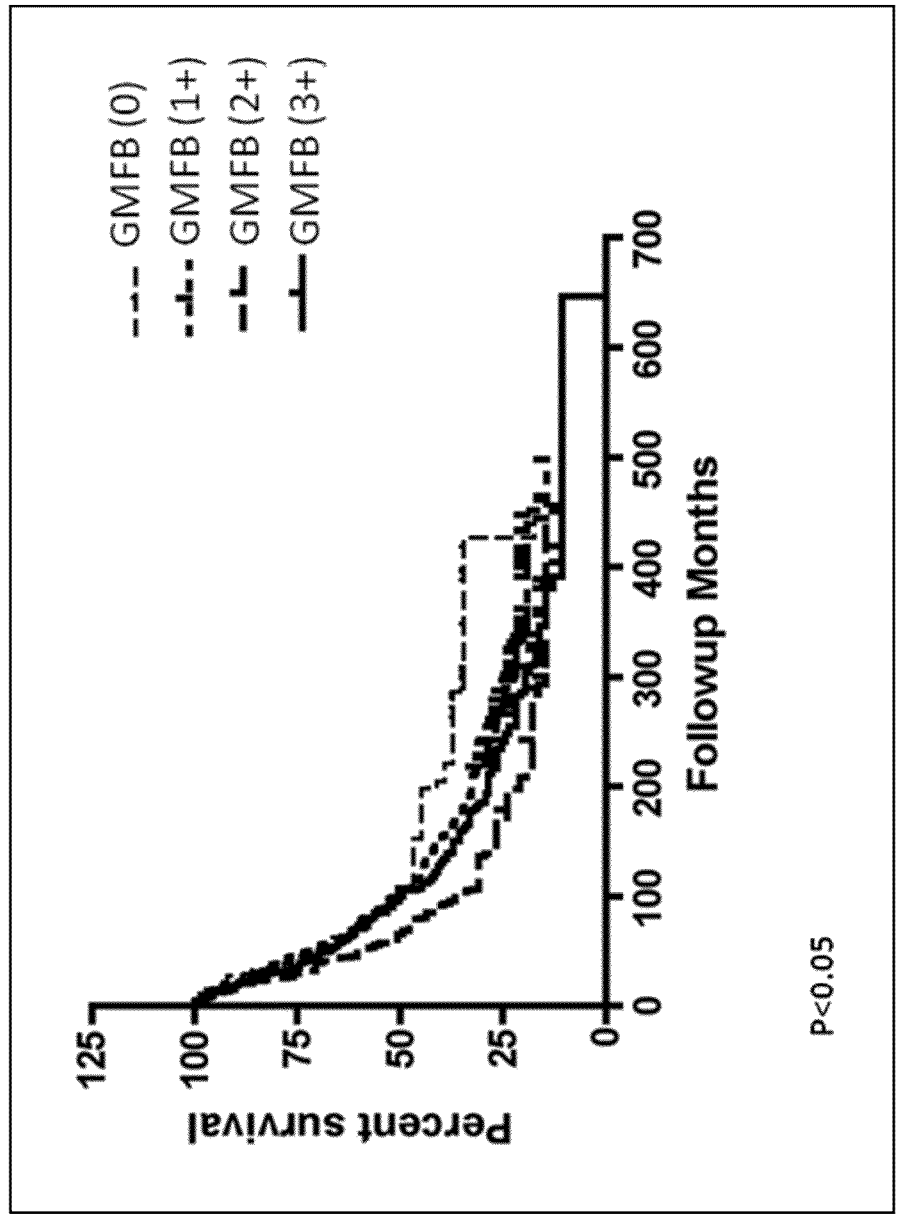

Alper-GMF-B is Significantly Associated with Increased Survival, with Higher Levels Associated with Longer Survival A total of 714 breast tumor and control samples are obtained from Yale School of Medicine, Department of Pathology, Tissue Microarray and Archiving, YTMA 49(9-10). Of these samples, 630 are from female breast cancer patients. These are the samples utilized for assessment and sGMF-B levels are measured with an ELISA assay using anti-sGMF-B mAb (clone name: Alper-GMF-B). Available patient characteristics are examined for any association with overall survival time using the long rank test. Overall survival was measured as the number of months from diagnosis to death or last contact. Patients without dates of death were censored on their date of last contact. Nuclear grade was omitted from multivariable analyses due to the number of samples missing this information. Non-significant variables were removed one at a time until all variables in the model were significant at the 0.05 level. Kaplan-Meier plots present the estimated survival for measures of GMF-B. FIG. 5 presents the overall survival curve for the whole population for GMF-B status, showing standard immunohistochemical (IHC) staining scores GMF-B (0), (1+), (2+), (3+). All patients have died or have last follow-up by 500 months except for one patient who died after 660 months. The curve is presented only to 500 months due to this gap. As shown in FIG. 5, anti-sGMF-B mAb (clone name: Alper-GMF-B) is significantly associated with increased survival, with higher levels associated with longer survival.

Example 8 sGMF-B has a Role in Neurodegenerative Disease State, and can Serve as a Biomarker for Detection and Progression of Alzheimer's Disease (AD)

Plasma samples obtained from AD age matched control and early, mid and late stage patient groups were diluted with PBS at a ratio of 1:10 (see FIG. 4A). Plasma GMF-B levels are measured with an enzyme-linked immunosorbent enzyme assay. The medisorp and polysorp ELISA plates (Nalgen NUNC® International, Rochester, N.Y.) were coated with 100 µl/well of diluted plasma and incubated at 4° C. overnight. The plasma samples are analyzed in a blinded fashion. The wells are washed with PBS and incubated at room temperature for one hour with blocking buffer (5% BSA in PBS). After washing with PBS, the primary antibody, anti-sGMF-B mAb (clone name: Alper-sGMF-B) is added in dilution buffer (45 µg/ml) (PBS buffer, 1% BSA, 0.01% Tween-20). Wells are washed with PBS/0.03% Tween-20 and incubated at room temperature for one hour with 100 µl/well secondary antibody (HRP-Donkey anti-mouse IgG, Jackson ImmunoResearch, West Grove, Pa.) diluted 1:3000. After washing the wells, 100 µl Immunopure TMB substrate solution (Pierce, Rockford, Ill.) is added. The color reaction is stopped by the addition of 100 µl/well 1N $H_2SO_4$ and analysis is performed with an ELISA Reader. Optical density is represented by OD and shows sGMF-B levels in plasma. See FIG. 6.

Figure 6:
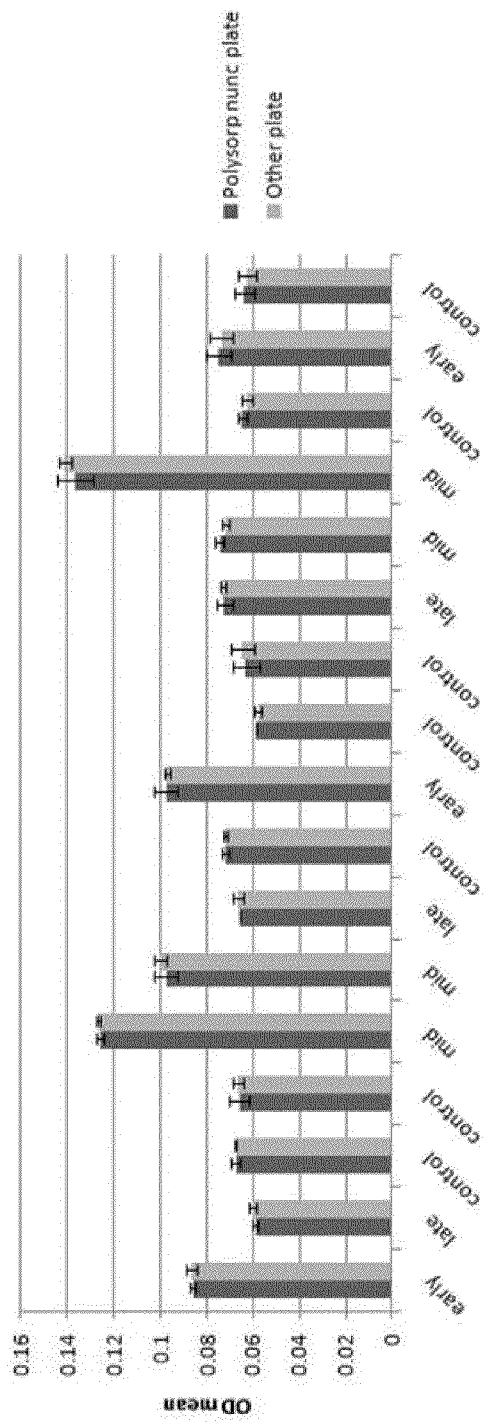

FIG. 6 shows results from one-step ELISA analysis of blood samples from patients with early, mid and late stages of AD compared to age-matched healthy controls using Alper-sGMF-B mAb. There is an increase in levels of sGMF BETA in blood samples from most patients with early, mid and late stages of AD compared to age-matched healthy controls. The levels for sGMF BETA show a gradual increase in early and mid-stages of AD using Alper-sGMF-B mAb. The level of sGMF BETA at late stages of AD is similar to healthy control levels. Levels of sGMF BETA show significant increases in early and mid-stage AD blood samples. The p-values derived using Mann Whitney Test showed a significant difference among control, early and mid stage $p<0.001$ in FIGS. 6B-1 and 6B-2.

Example 9

Evaluation of Plasma Samples

GMF-B is evaluated in subject patient plasma samples from early, mid, and late stage AD patients, non-AD dementia patients and healthy controls using an ELISA assay using anti-sGMF-B mAb (clone name: Alper-GMF-B) to validate the sensitivity and specificity of GMF-B as a biomarker for early and mid-stage Alzheimer's disease.

Example 10

Alper-sGMF-B Heavy Chain Antibody Sequence

Framework Regions (FWRs) and Complementarity Determining Regions (CDRs) of the heavy chain of the GMF-B mAb, in which the polypeptide sequence provided below the polynucleotide sequence corresponds to the sequence of the GMF-B mAb. Amino acid residues are numbered using the convention of Kabat et al. The bold residues set forth in underlined text indicate the specificity determining residues (SDRs). See FIG. 7 and SEQ ID NO: 1.

Example 11

Alper-sGMF-B Heavy Chain Antibody Sequence

FWRs and CDRs of the light chain of the sGMF-B mAb, Alper-sGMF-B mAb, in which the polypeptide sequence provided below the polynucleotide sequence corresponds to the sequence of the GMF-B mAb. Amino acid residues are numbered using the convention of Kabat et al. The bold residues set forth in underlined text indicate the specificity determining residues (SDRs). See FIG. 8 and SEQ ID NO: 5.

What has been described and illustrated herein are exemplary embodiments of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims, in which all terms are meant in their broadest reasonable sense unless otherwise indicated therein.

What is claimed is:

1. An isolated antibody or antibody fragment specific for glia maturation factor beta (GMF-B), comprising a heavy chain variable domain comprising three complementarity determining regions (CDRs) comprising the amino acid sequences of SEQ ID NO: 2, SEQ ID NO:3, and SEQ ID NO: 4, and a light chain variable domain comprising three CDRs comprising the amino acid sequences of SEQ ID NO: 6, SEQ ID NO:7, and SEQ ID NO: 8.

2. The antibody or antibody fragment of claim 1, wherein the heavy chain comprises SEQ ID NO: 1, and the light chain comprises SEQ ID NO: 5.

3. The antibody or antibody fragment of claim 1, wherein the antibody or antibody fragment is capable of preferentially binding to GMF-B in its soluble form and/or its secreted form, wherein the preferential binding is relative to a nuclear form of GMF-B.

4. The antibody or antibody fragment of claim 1, wherein the soluble form of GMF-B has a molecular weight of about 17 kilodaltons as measured by gradient polyacrylamide gel electrophoresis.

5. The antibody or antibody fragment of claim 1, wherein the antibody or antibody fragment is capable of selectively reducing the activity of GMF-B.

6. The antibody or antibody fragment of claim 1, wherein the antibody or antibody fragment is capable of binding GMF-B with an affinity of between $10^{-8}$ and $10^{-11}$ M.

7. The antibody or antibody fragment of claim 1, wherein the antibody or antibody fragment is capable of recognizing at least one epitope selected from the group consisting of SEQ ID NOs: 15, 16, and 17, and fragments thereof.

8. The antibody or antibody fragment of claim 1, wherein the antibody or antibody fragment is immobilized on a solid phase.

9. The antibody or antibody fragment of claim 1, wherein the antibody or antibody fragment is conjugated to an agent selected from the group consisting of a detectable label, a cytotoxic radionuclide, a cytotoxic drug, and a cytotoxic protein.

10. The antibody or antibody fragment of claim 1, wherein the antibody or antibody fragment is humanized.

11. A kit comprising the antibody or antibody fragment of claim 1 and a secondary antibody conjugated to a detectable label, or the antibody or antibody fragment of claim 1 that is further modified to be detectably labeled.

12. An immunoassay for detecting GMF-B in a biological sample wherein biological sample is contacted with the antibody or antibody fragment of claim 1, and the formation of an immune complex with GMF-B is qualitatively or quantitatively determined.

13. The immunoassay of claim 12, wherein the biological sample is a human cell or tissue sample selected from breast, ovary, cervix, prostate, colon, stomach, kidney, liver, head, neck, lung, blood, pancreas, skin, testis, thyroid, and brain.

14. The immunoassay of claim 12, wherein the biological sample is selected from the group consisting of blood, plasma, urine, serum, tissue, and cell.

15. The immunoassay of claim 14, wherein the cell or tissue sample is cancerous.

16. The immunoassay of claim 14, wherein the blood, plasma, urine, or serum comprises circulating tumor cells.

17. The immunoassay of claim 12, wherein the immunoassay is selected from the group consisting of ELISA, immunohistochemistry, and immunofluorescence.

18. The immunoassay of claim 12, wherein the level of immune complex detected correlates positively with expected survival time.

* * * * *

UNITED STATES PATENT AND TRADEMARK OFFICE
CERTIFICATE OF CORRECTION

| | | |
|---|---|---|
| PATENT NO. | : 8,519,104 B2 | Page 1 of 1 |
| APPLICATION NO. | : 12/944510 | |
| DATED | : August 27, 2013 | |
| INVENTOR(S) | : Özge Alper | |

It is certified that error appears in the above-identified patent and that said Letters Patent is hereby corrected as shown below:

Title page, item (75), col. 1, under "Inventor:"

"Ozge Alper" should read as --- Özge Alper

Signed and Sealed this
Nineteenth Day of November, 2013

Teresa Stanek Rea
*Deputy Director of the United States Patent and Trademark Office*